United States Patent
Imran

(10) Patent No.: US 8,983,624 B2
(45) Date of Patent: Mar. 17, 2015

(54) DELIVERY DEVICES, SYSTEMS AND METHODS FOR STIMULATING NERVE TISSUE ON MULTIPLE SPINAL LEVELS

(75) Inventor: Mir A. Imran, Los Altos, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 1169 days.

(21) Appl. No.: 11/952,053

(22) Filed: Dec. 6, 2007

(65) Prior Publication Data

US 2008/0140169 A1    Jun. 12, 2008

Related U.S. Application Data

(60) Provisional application No. 60/873,535, filed on Dec. 6, 2006, provisional application No. 60/873,464, filed on Dec. 6, 2006.

(51) Int. Cl.
*A61N 1/05* (2006.01)
*A61N 1/36* (2006.01)

(52) U.S. Cl.
CPC ............. *A61N 1/0551* (2013.01); *A61N 1/3605* (2013.01); *A61N 1/05* (2013.01); *A61N 1/36071* (2013.01); *A61N 1/0558* (2013.01)
USPC ............................... 607/117; 607/46; 607/116

(58) Field of Classification Search
CPC ............ A61N 1/36021; A61N 1/3605; A61N 1/3606; A61N 1/36071; A61N 1/05; A61N 1/0551; A61N 1/0558
USPC ............................. 607/2, 3, 45, 46, 115–118
See application file for complete search history.

(56) References Cited

U.S. PATENT DOCUMENTS

| 525,891 A | 9/1894 | Fricke |
| 3,724,467 A | 4/1973 | Avery et al. |
| 3,845,770 A | 11/1974 | Theeuwes et al. |
| 3,916,899 A | 11/1975 | Theeuwes et al. |
| 4,141,367 A | 2/1979 | Ferreira |
| 4,232,679 A | 11/1980 | Schulman |

(Continued)

FOREIGN PATENT DOCUMENTS

| CN | 2401143 Y | 10/2000 |
| CN | 101594907 A | 12/2009 |

(Continued)

OTHER PUBLICATIONS

Kim et al.; U.S. Appl. No. 12/369,706 entitled "Methods for stimulating a dorsal root ganglion," filed Feb. 11, 2009.

(Continued)

*Primary Examiner* — Eric D. Bertram
*Assistant Examiner* — Pamela M Bays
(74) *Attorney, Agent, or Firm* — Shay Glenn LLP

(57) ABSTRACT

Devices, systems and methods are provided for simultaneously stimulating the spinal anatomy at various locations, such as spinal levels, along the spinal cord. By stimulating multiple levels of the spinal column with the use of a single device, a single access path is created to an implantable pulse generator (IPG) rather than individual access paths for each lead at each spinal level to an IPG. By reducing the number of pathways, the procedure complexity, time and recovery are reduced. In addition, some embodiments provide additional specificity within each targeted level, such as selective stimulation of specific tissue, such as the dorsal root ganglion.

39 Claims, 14 Drawing Sheets

(56) References Cited

U.S. PATENT DOCUMENTS

| | | | |
|---|---|---|---|
| 4,298,003 A | 11/1981 | Theeuwes et al. |
| 4,313,448 A | 2/1982 | Stokes |
| 4,374,527 A | 2/1983 | Iversen |
| 4,479,491 A | 10/1984 | Martin |
| 4,549,556 A | 10/1985 | Tarjan et al. |
| 4,573,481 A | 3/1986 | Bullara |
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,419,763 A * | 5/1995 | Hildebrand ............... 604/517 |
| 5,458,626 A | 10/1995 | Krause |
| 5,489,294 A | 2/1996 | McVenes et al. |
| 5,505,201 A | 4/1996 | Grill, Jr. et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,720,099 A | 2/1998 | Parker et al. |
| 5,733,322 A | 3/1998 | Starkebaum |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A | 9/1999 | Moumane et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,425,887 B1 * | 7/2002 | McGuckin et al. ............ 604/272 |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,047,082 B1 | 5/2006 | Schrom et al. |
| 7,096,070 B1 | 8/2006 | Jenkins et al. |
| 7,127,287 B2 | 10/2006 | Duncan et al. |
| 7,181,289 B2 | 2/2007 | Pflueger et al. |
| 7,333,857 B2 | 2/2008 | Campbell |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 | 6/2002 | Clemens et al. |
| 2002/0087113 A1 | 7/2002 | Hartlaub |
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 | 10/2002 | Soukup et al. |
| 2002/0198527 A1 | 12/2002 | Muckter |
| 2003/0018367 A1 | 1/2003 | DiLorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler, III et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0172089 A1 | 9/2004 | Whitehurst et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |

(56) References Cited

U.S. PATENT DOCUMENTS

| | | |
|---|---|---|
| 2004/0230280 A1 | 11/2004 | Cates et al. |
| 2004/0236388 A1* | 11/2004 | Gielen et al. .................... 607/48 |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052826 A1 | 3/2006 | Kim et al. |
| 2006/0052827 A1 | 3/2006 | Kim et al. |
| 2006/0052828 A1 | 3/2006 | Kim et al. |
| 2006/0052835 A1 | 3/2006 | Kim et al. |
| 2006/0052836 A1 | 3/2006 | Kim et al. |
| 2006/0052837 A1 | 3/2006 | Kim et al. |
| 2006/0052838 A1 | 3/2006 | Kim et al. |
| 2006/0052839 A1* | 3/2006 | Kim et al. ................. 607/48 |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | De Ridder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0206118 A1 | 9/2006 | Kim et al. |
| 2006/0241716 A1 | 10/2006 | Finch et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1* | 9/2007 | Hiatt .................... 604/164.01 |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0154349 A1 | 6/2008 | Rossing et al. |
| 2008/0188916 A1 | 8/2008 | Jones et al. |
| 2009/0204173 A1 | 8/2009 | Fang et al. |
| 2010/0179562 A1 | 7/2010 | Linker et al. |
| 2010/0249875 A1 | 9/2010 | Kishawi et al. |
| 2011/0184486 A1 | 7/2011 | De Ridder |
| 2011/0257693 A1 | 10/2011 | Burdulis |
| 2011/0276056 A1 | 11/2011 | Grigsby et al. |
| 2012/0158094 A1 | 6/2012 | Kramer et al. |
| 2012/0283697 A1 | 11/2012 | Kim et al. |
| 2012/0310140 A1 | 12/2012 | Kramer et al. |
| 2013/0345783 A1 | 12/2013 | Burdulis |

FOREIGN PATENT DOCUMENTS

| | | |
|---|---|---|
| CN | 101678204 A | 3/2010 |
| EP | 0779080 | 6/1997 |
| EP | 1304135 A2 | 4/2003 |
| JP | 03041191 B2 | 6/1991 |
| JP | H06-218064 A | 8/1994 |
| JP | 8080353 A | 3/1996 |
| JP | 10243954 A | 4/1998 |
| JP | 2004512105 | 4/2004 |
| JP | 2006523215 | 10/2004 |
| JP | 2005516697 | 6/2005 |
| JP | 2008526299 | 7/2008 |
| JP | 2009539425 A | 11/2009 |
| JP | 2009539426 A | 11/2009 |
| WO | WO 02/096512 A1 | 12/2002 |
| WO | WO 03/018113 A1 | 3/2003 |
| WO | WO 03/043690 A1 | 5/2003 |
| WO | WO 03/063692 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |

OTHER PUBLICATIONS

Nannini et al.; Muscle recruitment with intrafascicular electrodes; IEEE Trans on Biomedical Engineering; vol. 38; No. 8; pp. 769-776 Aug. 1991.

Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.

Brounstein et al.; U.S. Appl. No. 12/780,696 entitled "Methods, systems and devices for neuromodulating spinal anatomy," filed May 14, 2010.

Kocsis at al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.

Lopez at al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; 2001.

Abdulla et al.; Axotomy- and autotomy-induced changes in the excitability of rat dorsal root ganglion neurons; J Neurophysiol; 85(2); pp. 630-643; Feb. 2001.

Burton et al.; The organization of the seventh lumbar spinal ganglion of the cat; J Comp Neurol.; 149(2); pp. 215-232; May 15, 1973.

Ma et al.; Enhanced excitability of dissociated primary sensory neurons after chronic compression of the dorsal root ganglion in the rat; Pain; 113(1-2); pp. 106-112; Jan. 2005.

Myles et al.; Effects of different methods of peripheral nerve repair on the number and distribution of muscle afferent neurons in rat dorsal root ganglion; J Neurosurg; 77(3); pp. 457-462; Sep. 1992.

Prats-Galino et al.Prats; Representations of hindlimb digits in rat dorsal root ganglia; J Comp Neurol; 408(1); pp. 137-145; May 24 1999.

Waxman et al.; Sodium channels, excitability of primary sensory neurons, and the molecular basis of pain; Muscle Nerve; 22(9); pp. 1177-1187; Sep. 1999.

Wessels et al.; A rostrocaudal somatotopic organization in the brachial dorsal root ganglia of neonatal rats; Clin Neurol Neurosurg; 95 Suppl; pp. S3-11; 1993.

Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.

Wessels et al.; Somatotopic organization in the sensory innervation of the rat hindlimb during development, using half dorsal root ganglia as subsegmental units; Eur J Morphol; 28(2-4); pp. 394-403; 1990.

Wessels et al.; The rostrocaudal organization in the dorsal root ganglia of the rat: a consequence of plexus formation?; Anat Embryol (Berl); 190(1); pp. 1-11; Jul. 1994.

Imran et al.; U.S. Appl. No. 12/607,009 entitled "Selective stimulation systems and signal parameters for medical conditions," filed Oct. 27, 2009.

Imran et al; U.S. Appl. No. 11/952,062 entitled "Implantable flexible circuit leads and methods of use," filed Dec. 6, 2007.

(56) References Cited

OTHER PUBLICATIONS

Burdulis, Albert; U.S. Appl. No. 11/952,065 entitled "Expandable stimulation leads and methods of use," filed Dec. 6, 2007.
Imran, Mir; U.S. Appl. No. 11/952,049, entitled "Grouped leads for spinal stimulation," filed Dec. 6, 2006.
Burdulis, Albert; U.S. Appl. No. 11/952,081 entitled "Hard tissue anchors and delivery devices," filed Dec. 6, 2007.
Imran et al; U.S. Appl. No. 12/022,135 entitled "Sutureless lead retention features," filed Jan. 29, 2008.
Advanced Neuromodulation Systems, Inc. (ANSI) Research Briefing dated Aug. 20, 2004 by Stephens Inc. Investment Bankers pp. 1-4.
Advanced Neuromodulation Systems, Inc. (ANSI) Research Bulletin dated Jul. 2, 2004 by Stephens Inc. Investment Bankers pp. 1-7.
Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. 2002. New Trends in Neuromodulation for the Management of Neuropathic Pain. Neurosurgery. 50 (4): 690-703.
Aoki, Yasuchika et al. 2004. Distribution and Immunocytochemical Characterization of Dorsal Root Ganglion Neurons Innervating the Lumbar Intervertebral Disc in Rats: a Review. Life Sciences. 74 (21): 2627-2642.
Askar, Zahid, et al. 2003. Scott Wiring for Direct Repair of Lumbar Spondylolysis. Spine. 28 (4): 354-357.
Baba, Hiroshi et al. 1999. Peripheral Inflammation Facilitates a? Fiber-Mediated Synaptic Input to the Substantia Gelatinosa of the Adult Rat Spinal Cord. The Journal of Neuroscience. 19 (2): 859-867.
Bajwa, Zahid H. et al. 2001. Herpetic Neuralgia: Use of Combination Therapy for Pain Relief in Acute and Chronic Herpes Zoster. Geriatrics. 56 (12): 18-24.
Barendse, G.A. et al. 2001. Randomized Controlled Trial of Percutaneo Intradiscal Radiofrequency Thermocoagulation for Chronic Discogenic Back Pain: Lack of Effect From a 90-Second 70 C Lesion. Spine. 26 (3): 287-92. (Abstract Only).
Barlocher, C.B. et al. 2003. Kryorhizotomy: an Alternative Technique for Lumbar Medial Branch Rhizotomy in Lumbar Facet Syndrome. J Neurosurg. 98 (1): 14-20. (Abstract Only).
Blau, A. et al. 1997. Characterization and Optimization of Microelectrode Arrays for in Vivo Nerve Signal Recording and Stimulation. Biosens Bioelectron.12 (9-10): 883-92. (Abstract Only).
Boston Scientific a Neuromodulation Primer dated Jun. 9, 2004 in Medical Supplies and Devices, published by Susquehanna Financial Group, LLLP pp. 1-17.
Brammah, T.B. et al, 1994. Syringomyelia as a Complication of Spinal Arachnoiditis. Spine. 19 (22): 2603-5. (Abstract Only).
Braverman D.L. et al. 2001. Using Gabapentin to Treat Failed Back Surgery Syndrome Caused by Epidural Fibrosis: a Report of 2 Cases. Arch Phys Med Rehabil. 82 (5): 691-3. (Abstract Only) •.
Carlton, Susan M. et al. 2001. Tonic Control of Peripheral Cutaneo Nociceptors by Somatostatin Receptors. Journal of Neuroscience. 21 (11): 4042-4049.
Chaplan, S.R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by Nerve Cuff Electrodes. IEEE Transactions on Rehabilitation Engineering. 8 (1): 35-41.
Cyberonics, Inc. Equity Research dated Jan. 16, 2003 by Pacific Growth Equities pp. 1-14.
Denny, N.M. et al. 2003. Evaluation of an Insulated Tuohy Needle System for the Placement of Interscalene Brachial Plex Catheters. Anaesthesia. 58 (6): 554-7. (Abstract Only).

Dreyfuss, Paul et al. 2000. Efficacy and Validity of Radiofrequency Neurotomy for Chronic Lumbar Zygapophysial Joint Pain. Spine. 25 (10): 1270-1277.
Dubuisson, D. 1995. Treatment of Occipital Neuralgia by Partial Posterior Rhizotomy at C1-3. J Neurosurg. 82 (4): 581-6. (Abstract Only).
Eschenfelder, Sebastian et al. 2000. Dorsal Root Section Elicits Signs of Neuropathic Pain Rather than Reversing Them in Rats With L5 Spinal Nerve Injury. Pain. 87 (2): 213-219.
Firth, Ava et al. 1999. Development of a Scale to Evaluate Postoperative Pain in Dogs. J Am Vet Med Assoc. 214 (5): 651-659.
Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J Neurosurg. 61 (5): 952-5. (Abstract Only).
Gocer, A.I. et al. 1997. Percutaneo Radiofrequency Rhizotomy of Lumbar Spinal Facets the Results of 46 cases. Neurosurg Rev. 20 (2): 114-6. (Abstract Only).
Haller, H. et al. Treatment of Chronic Neuropathic Pain After Traumatic Central Cervical Cord Lesion with Gabapentin. Journal of Neural Transmission. 110 (9): 977-981.
Herron, L.D. 1989. Selective Nerve Root Block in Patient Selection for Lumbar Surgery: Surgical Results. J Spinal Disord. 2 (2): 75-9. (Abstract Only).
Higuchi, Yoshinori, et al. 2002. Exposure of the Dorsal Root Ganglion in Rats to Pulsed Radiofrequency Currents Activates Dorsal Horn Lamina I and II Neurons. Neurosurgery. 50 (4): 850-856.
Holsheimer, J. et al. 1995. Effects of Electrode Geometry and Combination on Nerve Fibre Selectivity in Spinal Cord Stimulation. Medical & Biological Engineering & Computing. 33 (5): 676-682.
Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181.
Julius, David et al. 2001. Molecular Mechanisms of Nociception. Nature. 413 (6852): 203-210.
Kanpolat, Yucel et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.
Kapadia, N.P. et al. 2000. Gabapentin for Chronic Pain in Spinal Cord Injury: A Case Report. Arch Phys Med Rehabil. 81 (10): 1439-41. (Abstract Only).
Kapoor, Vibhu et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.
Karat, Laszlo et al. 2004. Deletion of Vanilloid Receptor 1-Expressing Primary Afferent Neurons for Pain Control. Journal of Clinical Investigation. 113 (9): 1344-1352.
Kline, David G. et al. 1998. Management and Results of Sciatic Nerve Injuries: a 24-Year Experience. Journal of Neurosurgery. 89 (1): 13-23.
Kobayashi, Shigeru et al. 2004. Pathology of Lumbar Nerve Root Compression Part 1: Intraradicular Inflammatory Changes Induced by Mechanical Compression. Journal of Orthopaedic Research. 22 (1): 170-179.
Kobayashi, Shigeru et al. 2004. Pathology of Lumbar Nerve Root Compression Part 2: Morphological and Immunohistochemical Changes of Dorsal Root Ganglion. Journal of Orthopaedic Research. 22(1): 180-188.
Koszewski, W. et al. 2003. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only).
Lawrence, Stephen M. et al. 2002. Long-Term Biocompatibility of Implanted Polymer-Based Intrafascicular Electrodes. Journal of Biomedical Materials Research. 63 (5): 501-506.
Lee, In-Seop et al. 2002. Characterization of Iridium Film as a Stimulating Neural Electrode. Biomaterials. 23 (11):2375-2380.

(56) References Cited

OTHER PUBLICATIONS

Lew, Henry L. et al. 2004. Preganglionic Approach to Transforaminal Epidural Steroid Injections. Am. J. Phys. Med. Rehabil. 83 (5): 378.
Maher, C.O. et al. 1999. Lateral Exit-Zone Stenosis and Lumbar Radiculopathy. J Neurosurg. 90 (1): 52-8. (Abstract Only).
Mailley, Sophie et al. 2004. Thin Film Platinum Cuff Electrodes for Neurostimulation: In Vitro Approach of Safe Neurostimulation Parameters. Bioelectrochemistry. 63: 359-364.
Masin I, Michelle et al. 1996. Activated Pyrolytic Carbon Tip Pacing Leads: An Alternative to Steroid-Eluting Pacing Leads? PACE. 1: 1832-1835.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html. (accessed Feb. 24, 2006).
Mond, Harry G. et al. 2004. Implantable Transveno Pacing Leads: The Shape of Things to Come. PACE. 27: 887-893.
Monti, Enrico. 2004. Peripheral Nerve Stimulation: A Percutaneo Minimally Invasive Approach. Neuromodulation. 7 (3): 193. (Abstract Only).
Naples, Gregory G. 1988. A Spiral Nerve Cuff Electrode for Peripheral Nerve Stimulation. IEEE Transactions on Biomedical Engineering. 35 (11): 905-916.
Narozny, Martin et al. 2001. Therapeutic Efficacy of Selective Nerve Root Blocks in the Treatment of Lumbar Radicular Leg Pain. Swiss Med Wkly. 131 (5-6): 75-80.
Nashold, Blaine S. et al. 1979. Peripheral Nerve Stimulation for Pain Relief Using a Multicontact Electrode System. Technical note. Journal of Neurosurgery. 51 (6): 872-873.
Nashold, Blaine S. 1982. Long-Term Pain Control by Direct Peripheral-Nerve Stimulation. The Journal of Bone and Joint Surgery. 64 (1): 1-10.
Neumann, Simona et al. 2002. Regeneration of Sensory Axons Within the Injured Spinal Cord Induced by Intraganglionic cAMP Elevation. Neuron. 34 (6): 885-93.
Nielson, K.D. et al. 1976. Peripheral Nerve Injury From Implantation of Chronic Stimulating Electrodes for Pain Control. Surg Neurol. 5 (1): 51-3. (Abstract Only).
North, Richard B. et al. 1991. Dorsal Root Ganglionectomy for Failed Back Surgery Syndrome: a 5-Year Follow-Up Study. J Neurosurg. 74: 236-242.
North, Richard B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.
Nygaard, Oystein P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.
Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.
Obata, Koichi, et al. 2002. Expression of Neurotrophic Factors in the Dorsal Root Ganglion in a Rat Model of Lumbar Disc Herniation. Pain. 99 (1-2): 121-132.
Olby, Natasha J. et al. 2001. Development of a Functional Scoring System in Dogs With Acute Spinal Cord Injuries. Am J Vet Res. 62 (10): 1624-1628.
Parlier-Cuau, Caroline et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.

Pedrolli, C. et al. 1990. [Dorsolumbar Arachnoid Cysts. A Case Report]. Recenti Prog Med. 81 (11): 699-701. (Abstract Only).
Rodriguez, Francisco J. et al. 2000. Polyimide Cuff Electrodes for Peripheral Nerve Stimulation. Journal of Neuroscience Methods. 98 (2): 105-118.
Rokugo, Tomoyuki et al. 2002. A Histochemical Study of Substance P in the Rat Spinal Cord: Effect of Transcutaneo Electrical Nerve Stimulation. J Nippon Med Sch. 69 (5): 428-433.
Romero, E. et al. 2001. Neural Morphological Effects of Long-Term Implantation of the Self-Sizing Spiral Cuff Nerve Electrode. Medical & Biological Engineering & Computing. 39 (1): 90-100.
Rongstad, K. et al. 1996. Popliteal Sciatic Nerve Block for Postoperative Analgesia. Foot Ankle Int. 17 (7): 378-82. (Abstract Only).
Ruetten, S. et al. 2003. Endoscopic Surgery of the Lumbar Epidural Space (Epiduroscopy): Results of Therapeutic Intervention in 93 Patients. Minim Invasive Neurosurg. 46 (1): 1-4. (Abstract Only).
Sairyo, K. et al. 2003. A New Endoscopic Technique to Decompress Lumbar Nerve Roots Affected by Spondylolysis. Technical Note. J Neurosurg. 98 (3): 290-3. (Abstract Only).
Salame, K. et al. 2003. Surgical Treatment of Spasticity by Selective Posterior Rhizotomy 30 Years Experience. Isr Med Assoc J. 5 (8): 543-6. (Abstract Only).
Saris, S.C. et al. 1986. Sacrococcygeal Rhizotomy for Perineal Pain. Neurosurgery. 19 (5): 789-93. (Abstract Only).
Sauvage, P.J. et al. 2000. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De.
Schwartzman, Robert J. et al. 2001. Neuropathic Central Pain: Epidemiology, Etiology, and Treatment Options. Arch Neurol. 58 (10): 1547-1550.
Sedan, R. et al. 1978. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.
Sheth, Rishi N. et al. 2002. Mechanical Hyperalgesia After an L5 Ventral Rhizotomy or an L5 Ganglionectomy in the Rat. Pain. 96: 63-72.
Siddall, Philip J. et al. 2004. Persistent Pain as a Disease Entity: Implications for Clinical Management. Anesth Analg. 99: 510-20.
Silvers, H.R. 1990. Lumbar Percutaneo Facet Rhizotomy. Spine.15 (1): 36-40. (Abstract Only).
Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).
Sluijter, Menno E. et al. 1998. The Effects of Pulsed Radiofrequency Fields Applied to the Dorsal Root Ganglion—A Preliminary Report. The Pain Clinic.11 (2): 109-117.
Smith, H.P. et al. 1981. Radiofrequency Neurolysis in a Clinical Model: Neuropathological Correlation. J Neurosurg. 55 (2): 246-53. (Abstract Only).
Spaic, M. et al. 1999. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312.
Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.
Stanton-Hicks, M. et al. 1997. Stimulation of the Central and Peripheral Nervo System for the Control of Pain. Journal of Clinical Neurophysiology. 14 (1): 46-62.
Steinbok, P. et al. 1998. Complications After Selective Posterior Rhizotomy for Spasticity in Children With Cerebral Palsy. Pediatr Neurosurg. 28 (6): 300-13. (Abstract Only).
Stolker, Robert J. et al. 1994. The Treatment of Chronic Thoracic Segmental Pain by Radiofrequency Percutaneo Partial Rhizotomy. J Neurosurg. 80 : 986-992.
Strait, T.A. et al. 1981. Intraspinal Extradural Sensory Rhizotomy in Patients With Failure of Lumbar Disc Surgery. J Neurosurg. 54 (2): 193-6. (Abstract Only).

(56) References Cited

OTHER PUBLICATIONS

Taha, J.M. et al. 1995. Long-Term Results of Radiofrequency Rhizotomy in the Treatment of Cluster Headache. Headache. 35 (4): 193-6. (Abstract Only).

Taub, Arthur et al. 1995. Dorsal Root Ganglionectomy for Intractable Monoradicular Sciatica: A Series of 61 Patients. Stereotact Funct Neurosurg. 65 (1-4): 106-110.

Uematsu, Sumio. 1988. Chapter 106: Percutaneo Electrothemnocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). P.

Van Zundert, Jan et al. 2005. Pulsed Radiofrequency in Chronic Pain Management: Looking for the Best Use of Electrical Current. World Institute of Pain. 5 (2): 74-76.

Van De Kraats, Everine B. et al. 2004. Noninvasive Magnetic Resonance to Three-Dimensional Rotational X-Ray Registration of Vertebral Bodies for Image-Guided Spine Surgery. Spine. 29 (3): 293-297.

Van Kleef, M. et al. 1993. Effects and Side Effects of a Percutaneo Thermal Lesion of the Dorsal Root Ganglion in Patients with Cervical Pain Syndrome. Pain. 52 (1): 49-53.

Van Kleef, M. et al. 1996. Radiofrequency Lesion Adjacent to the Dorsal Root Ganglion for Cervicobrachial Pain: a Prospective Double Blind Randomized Study. Neurosurgery. 38 (6): 1127-31.

Van Kleef, Maarten et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.

Van Zundert, J. et al. 2005. Pulsed and Continuo Radiofrequency Current Adjacent to the Cervical Dorsal Root Ganglion of the Rat Induces Late Cellular Activity in the Dorsal Horn. Anesthesiology. 102 (1): 125-31.

Vaughan, R. 1975. Percutaneo Radiofrequency Gangliotomy in the Treatment of Trigeminal Neuralgia and Other Facial Pain. Aust N Z J Surg. 45 (2): 203-7. (Abstract Only).

Viton, J.-M. et al. 1998. Short-Term Assessment of Periradicular Corticosteroid Injections in Lumbar Radiculopathy Associated With Disc Pathology. Neuroradiology. 40 (1): 59-62.

Viton, J.M. et al. 1998. Short-Term Evaluation of Periradicular Corticosteroid Injections in the Treatment of Lumbar Radiculopathy Associated With Disc Disease. Rev Rhum Engl Ed. 65 (3): 195-200. (Abstract Only).

Wagner, A.L. et al. 2002. Selective Nerve Root Blocks. Tech Vasc Intery Radiol. 5 (4): 194-200. (Abstract Only).

Weiner, Richard L. 2000. The Future of Peripheral Nerve Neurostimulation. Neurological Research. 22 (3): 299-304.

Weiner, Richard L. 2003. Peripheral Nerve Neurostimulation. Neurosurgery Clinics of North America. 14 (3): 401-408.

Weinstein, James et al. 1988. The Pain of Discography. Spine. 13(12):1344-8.

Wetzel, F. Todd et al. 1997. Extradural Sensory Rhizotomy in the Management of Chronic Lumbar Radiculopathy: A Minimum 2-Year Follow-up Study. Spine. 22 (19): 2283-2291.

Wetzel, F.T. 1992. Chronic Benign Cervical Pain Syndromes: Surgical Considerations. Spine. 17 (10): S367-74. (Abstract Only).

Wetzel, F.T. et al. 1992. The Treatment of Chronic Extremity Pain in Failed Lumbar Surgery. The Role of Lumbar Sympathectomy. Spine. 17 (12): 2367-8. (Abstract Only).

White, P.F. et al. 2003. The Use of a Continuo Popliteal Sciatic Nerve Block After Surgery Involving the Foot and Ankle: Does It Improve the Quality of Recovery? Anesth Analg. 97 (5): 1303-9. (Abstract Only).

Whitworth, Louis Anthony et al. 2002. Application of Spinal Ablative Techniques for the Treatment of Benign Chronic Painful Conditions. Spine. 27 (22): 2607-2612.

Wilkinson, H.A. et al. 2001. Sensory Ganglionectomy: Theory, Technical Aspects, and Clinical Experience. J Neurosurg. 95 (1): 61-6. (Abstract Only).

Wong, C.B. et al. 2002. Clinical Outcomes of Revision Lumbar Spinal Surgery: 124 Patient With a Minimum of Two Years of Follow-Up. Chang Gung Med J. 25 (3): 175-82. (Abstract Only).

Wright, Robert E. et al. 1998. Neurostimulation of the L2 Dorsal Root Ganglion for Intractable Disc Pain: Description of a Novel Technique. Presented at the IFESS.

Wu, Gang et al. 2001. Early Onset of Spontaneo Activity in Uninjured C-Fiber Nociceptors After Injury to Neighboring Nerve Fibers. Journal of Neuroscience. 21 (8): RC140.

Yamashita, Toshihiko et al. 2002. A Quantitative Analysis of Sensory Function in Lumbar Radiculopathy Using Current Perception Threshold Testing. Spine. 27 (14): 1567-1570.

Yoshida, Hirotoshi et al. 1997. Lumbar Nerve Root Compression Caused by Lumbar Intraspinal Gas: Report of Three Cases. Spine.22 (3): 348-351.

Young, R.F. 1996. Chapter 161: Dorsal Rhizotomy and Dorsal Root Ganglionectomy (pp. 3442-3451). Neurological Surgery 4th Edition. (Julian R. Youmans ed.). Philadelphia: W.B. Saunders Company.

Kim et al; U.S. Appl. No. 12/051,770 entitled "Neurostimulation system," filed Mar. 19, 2008.

Kim et al.; U.S. Appl. No. 13/402,786 entitled "Neurostimulation System," filed Feb. 22, 2012.

Kramer et al.; U.S. Appl. No. 13/458,697 entitled "Selective stimulation to modulate the sympathetic nervous system," filed Apr. 27, 2012.

Kim et al.; U.S. Appl. No. 13/706,100 entitled "Neurostimulation Methods and Systems," filed Dec. 5, 2012.

Dorsal Root Ganglion; www.biology-online.org/dDorsal_root_ganglion; downloaded Nov. 5, 2013; 4 pgs.

The Peripheral Nervous System; http://cnx.org/content/m44751/latest; downloaded Nov. 5, 2013; 7 pgs.

Wedley et al. Handbook of Clinical Techniques in the Management of Chronic Pain. Taylor & Francis; pp. 17-19. Nov. 27, 1996.

Kishawi et al.; U.S. Appl. No. 13/753,326 entitled "Pain management with stimulation subthreshold to parasthesia," filed Jan. 29, 2013.

Horsch, S. et al. Epidural spinal cord stimulation in the treatment of severe peripheral arterial occlusive disease; Annals of Vascular Surgery; 8(5): 468-74. Sep. 1994.

Mayfield Clinic for Brain & Spine; printed from http://www.mayfieldclinic.com/PE-AnatSpine.htm (last updated Jan. 2013); 7 pages.

medicinenet.com; Definition of Lateral; printed from http://www.medterms.com/script/main/art.asp?articlekey=6226 (on Jun. 4, 2014); 3 pages.

Kim et al.; U.S. Appl. No. 14/216,805 entitled "Neurostimulation System," filed Mar. 17, 2014.

\* cited by examiner

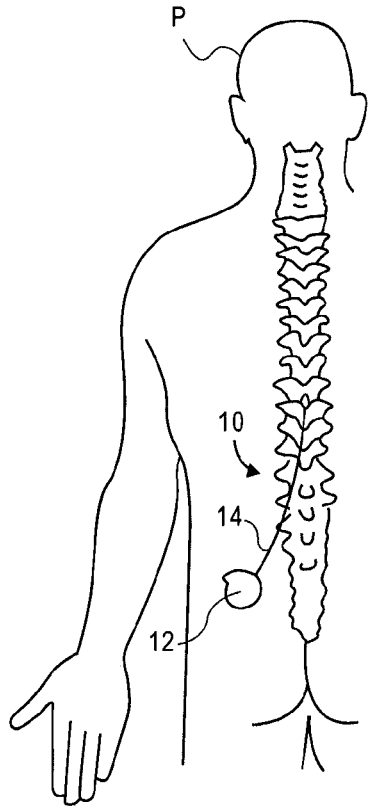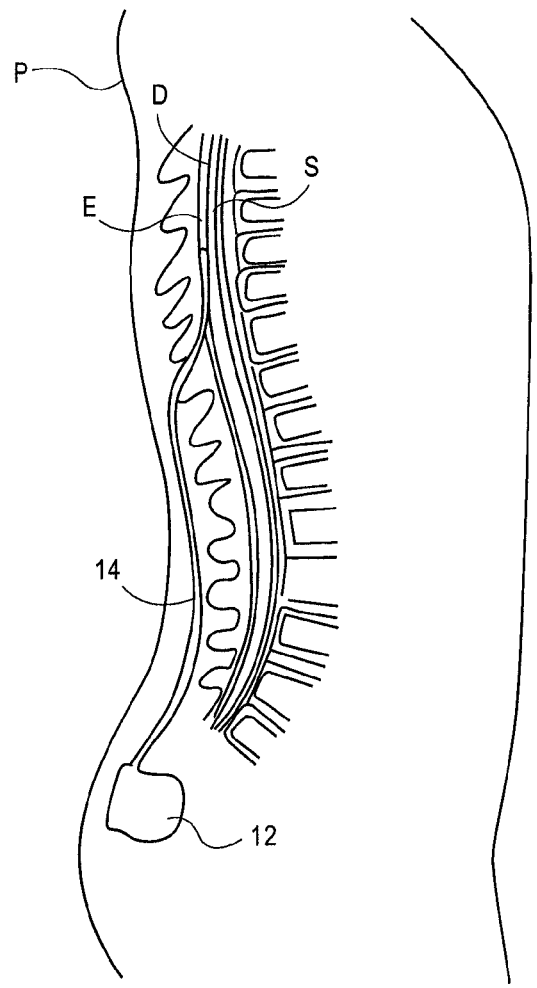
FIG. 1A
(PRIOR ART)
FIG. 1B
(PRIOR ART)

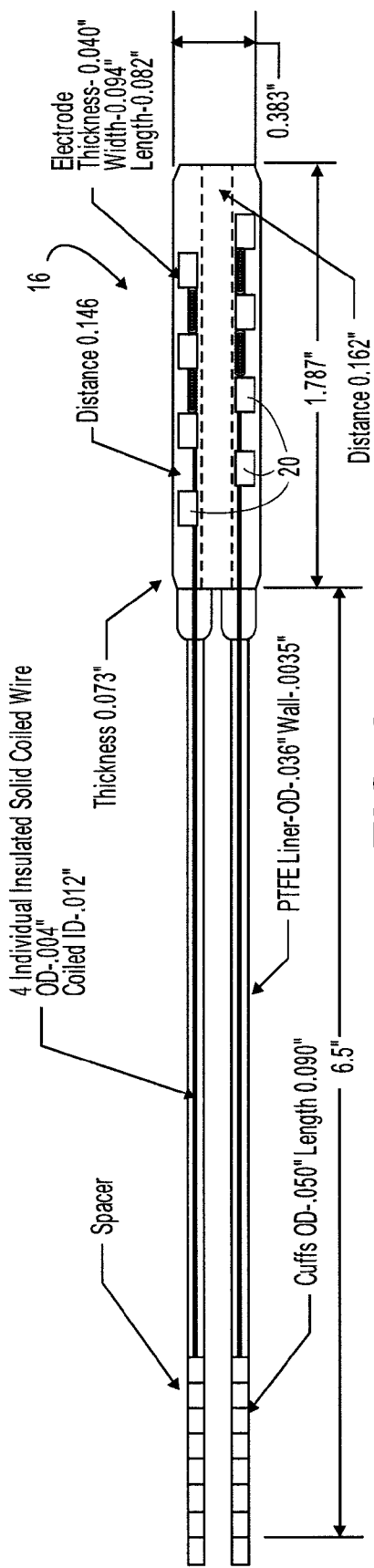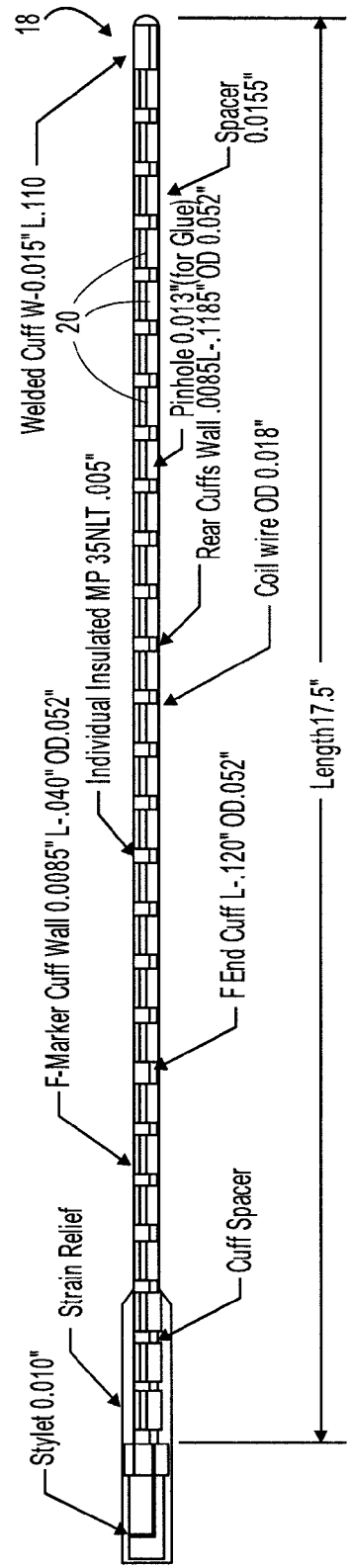
FIG. 3 (PRIOR ART)
FIG. 4 (PRIOR ART)

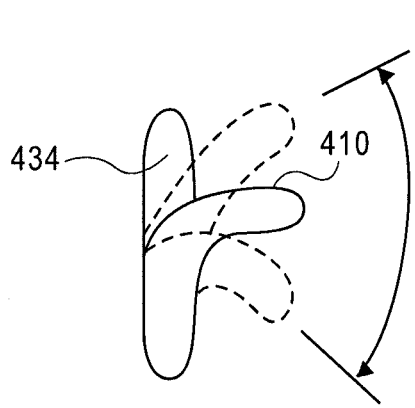
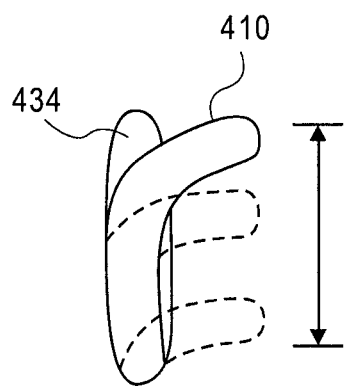
FIG. 9A  FIG. 9B
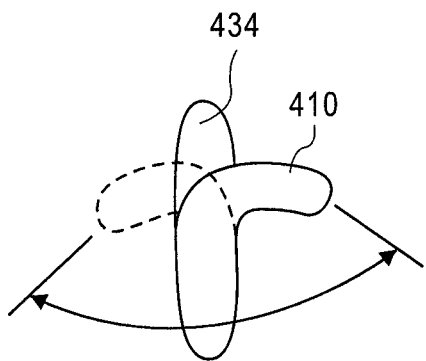
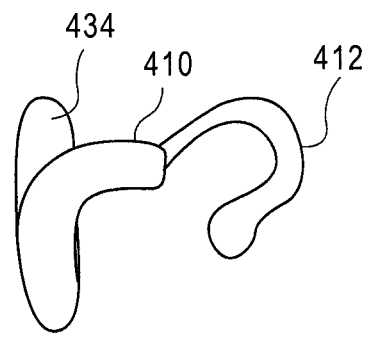
FIG. 9C  FIG. 10
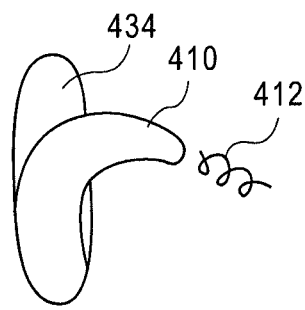
FIG. 11

DELIVERY DEVICES, SYSTEMS AND METHODS FOR STIMULATING NERVE TISSUE ON MULTIPLE SPINAL LEVELS

CROSS-REFERENCES TO RELATED APPLICATIONS

This application claims priority of provisional patent application No. 60/873,535, filed on Dec. 6, 2006, and provisional patent application No. 60/873,464, filed on Dec. 6, 2006, both of which are incorporated herein by reference for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The application of specific electrical energy to the spinal cord for the purpose of managing pain has been actively practiced since the 1960s. It is known that application of an electrical field to spinal nervous tissue can effectively mask certain types of pain transmitted from regions of the body associated with the stimulated nervous tissue. Such masking is known as paresthesia, a subjective sensation of numbness or tingling in the afflicted bodily regions. Application of electrical energy has been based on the gate control theory of pain. Published in 1965 by Melzack and Wall, this theory states that reception of large nerve fiber information, such as touch, sense of cold, or vibration, would turn off or close the gate to reception of painful small nerve fiber information. The expected end result would, therefore, be pain relief. Based on the gate control theory, electrical stimulation of large fibers of the spinal cord cause small fiber information to be reduced or eliminated at that spinal segment and all other information downstream from that segment would be reduced or eliminated as well. Such electrical stimulation of the spinal cord, once known as dorsal column stimulation, is now referred to as spinal cord stimulation or SCS.

FIGS. 1A-1B illustrate conventional placement of an SCS system 10. Conventional SCS systems include an implantable power source or implantable pulse generator (IPG) 12 and an implantable lead 14. Such IPGs 12 are similar in size and weight to pacemakers and are typically implanted in the buttocks of a patient P. Using fluoroscopy, the lead 14 is implanted into the epidural space E of the spinal column and positioned against the dura layer D of the spinal cord S, as illustrated in FIG. 1B. The lead 14 is implanted either through the skin via an epidural needle (for percutaneous leads) or directly and surgically through a mini laminotomy operation (for paddle leads).

FIG. 2 illustrates example conventional paddle leads 16 and percutaneous leads 18. Paddle leads 16 typically have the form of a slab of silicon rubber having one or more electrodes 20 on its surface. Example dimensions of a paddle lead 16 is illustrated in FIG. 3. Percutaneous leads 18 typically have the form of a tube or rod having one or more electrodes 20 extending therearound. Example dimensions of a percutaneous lead 18 is illustrated in FIG. 4.

Implantation of a percutaneous lead 18 typically involves an incision over the low back area (for control of back and leg pain) or over the upper back and neck area (for pain in the arms). An epidural needle is placed through the incision into the epidural space and the lead is advanced and steered over the spinal cord until it reaches the area of the spinal cord that, when electrically stimulated, produces a comfortable tingling sensation (paresthesia) that covers the patient's painful area. To locate this area, the lead is moved and turned on and off while the patient provides feedback about stimulation coverage. Because the patient participates in this operation and directs the operator to the correct area of the spinal cord, the procedure is performed with local anesthesia.

Implantation of paddle leads 16 typically involves performing a mini laminotomy to implant the lead. An incision is made either slightly below or above the spinal cord segment to be stimulated. The epidural space is entered directly through the hole in the bone and a paddle lead 16 is placed over the area to stimulate the spinal cord. The target area for stimulation usually has been located before this procedure during a spinal cord stimulation trial with percutaneous leads 18.

Although such SCS systems have effectively relieved pain in some patients, these systems have a number of drawbacks. To begin, as illustrated in FIG. 5, the lead 14 is positioned upon the spinal cord dura layer D so that the electrodes 20 stimulate a wide portion of the spinal cord and associated spinal nervous tissue. The spinal cord is a continuous body and three spinal levels of the spinal cord are illustrated. For purposes of illustration, spinal levels are sub-sections of the spinal cord S depicting that portion where the dorsal root DR and ventral root VR join the spinal cord S. The peripheral nerve N divides into the dorsal root DR and the dorsal root ganglion DRG and the ventral nerve root VR each of which feed into the spinal cord S. An ascending pathway 17 is illustrated between level 2 and level 1 and a descending pathway 19 is illustrated from level 2 to level 3. Spinal levels can correspond to the veterbral levels of the spine commonly used to describe the vertebral bodies of the spine. For simplicity, each level illustrates the nerves of only one side and a normal anatomical configuration would have similar nerves illustrated in the side of the spinal cord directly adjacent the lead.

Motor spinal nervous tissue, or nervous tissue from ventral nerve roots, transmits muscle/motor control signals. Sensory spinal nervous tissue, or nervous tissue from dorsal nerve roots, transmit pain signals. Corresponding dorsal and ventral nerve roots depart the spinal cord "separately"; however, immediately thereafter, the nervous tissue of the dorsal and ventral nerve roots are mixed, or intertwined. Accordingly, electrical stimulation by the lead 14 often causes undesirable stimulation of the motor nerves in addition to the sensory spinal nervous tissue.

Because the electrodes span several levels the generated stimulation energy 15 stimulates or is applied to more than one type of nerve tissue on more than one level. Moreover, these and other conventional, non-specific stimulation systems also apply stimulation energy to the spinal cord and to other neural tissue beyond the intended stimulation targets. As used herein, non-specific stimulation refers to the fact that the stimulation energy is provided to all spinal levels including the nerves and the spinal cord generally and indiscriminately. Even if the epidural electrode is reduced in size to simply stimulate only one level, that electrode will apply stimulation energy indiscriminately to everything (i.e. all nerve fibers and other tissues) within the range of the applied energy. Moreover, larger epidural electrode arrays may alter cerebral spinal fluid flow thus further altering local neural excitability states.

Another challenge confronting conventional neurostimulation systems is that since epidural electrodes must apply energy across a wide variety of tissues and fluids (i.e. CSF fluid amount varies along the spine as does pia mater thickness) the amount of stimulation energy needed to provide the desired amount of neurostimulation is difficult to precisely control. As such, increasing amounts of energy may be required to ensure sufficient stimulation energy reaches the desired stimulation area. However, as applied stimulation energy increases so too increases the likelihood of deleterious damage or stimulation of surrounding tissue, structures or neural pathways.

Improved stimulation systems and methods are desired that enable more precise and effective delivery of stimulation energy. At least some of these objectives will be met by the present invention.

BRIEF SUMMARY OF THE INVENTION

The present invention provides devices, systems and methods for simultaneously stimulating the spinal anatomy at various locations, such as spinal levels, along the spinal cord. The spinal cord is a continuous body and may be considered to include various spinal levels. For example, a spinal level may be considered a sub-section of the spinal cord wherein a dorsal root and ventral root join the spinal cord. Spinal levels may also correspond to the vertebral levels of the spine commonly used to describe the vertebral bodies of the spine. It may be desired to stimulate particular spinal levels, rather than blanketly stimulating a wide area, so as to more effectively treat pain symptoms and reduce deleterious side effects. The present invention provides devices, systems and methods for such targeted stimulation at various spinal levels. In addition, some embodiments provide additional specificity within each targeted level, such as selective stimulation of specific tissue, such as the dorsal root ganglion.

By stimulating multiple levels of the spinal column with the use of a single device, a single access path is created to an implantable pulse generator (IPG) rather than individual access paths for each lead at each spinal level to an IPG. By reducing the number of pathways, the procedure complexity, time and recovery are reduced. It may be appreciated that the devices, systems and methods of the present invention may also be used to stimulate other portions of the spinal anatomy or other anatomies.

In a first aspect of the present invention, a delivery device is provided for delivering elements to nerve tissue on different spinal levels. In one embodiment, the device comprises an elongate structure shaped for positioning within an epidural space, wherein the elongate structure has a first opening alignable with a first spinal level and a second opening concurrently alignable with a second spinal level. The elongate structure includes at least one lumen configured to allow passage of at least one element through the first opening toward nerve tissue on the first spinal level and passage of at least one element through the second opening toward nerve tissue on the second spinal level.

Optionally, the elongate structure may comprise a first portion having the first opening and a second portion having the second opening, wherein the first and second portions move relative to each other so as to adjust a distance between the openings. When the first and second spinal levels are not adjacent to each other, the first and second portions may be moved to provide appropriate alignment of the openings.

In some embodiments, the openings face lateral to a midline of the epidural space. In other embodiments, the openings face longitudinal to a midline of the epidural space. Optionally, the first opening faces a direction on the first spinal level and another opening faces in a substantially opposite direction on the first spinal level. In some embodiments, the distance between the openings is fixed.

Typically, the at least one lumen comprises an individual lumen extending to the first opening and an individual lumen extending to the second opening. However, the elements may extend through one or more common lumens. In some embodiments, the delivery device further comprises a mechanism to fix the at least one element in relation to the elongate structure.

The openings may have any suitable shape. In some embodiments, the first opening is shaped to allow longitudinal translation of the at least one element within the first opening. In such instances, the first opening may have an oblong shape.

In another aspect of the present invention, a system is provided for treating nerve tissue on different spinal levels. In some embodiments, the system comprises an elongate structure shaped for positioning within an epidural space, wherein the elongate structure has a first opening alignable with a first spinal level and a second opening concurrently alignable with a second spinal level. A first element is extendable through the first opening and positionable so as to treat nerve tissue on the first spinal level, and a second element is extendable through the second opening and positionable so as to treat nerve tissue on the second spinal level.

Typically, the first element comprises a lead having at least one electrode. In such embodiments, the first element may be positionable so as to selectively stimulate a dorsal root ganglion on the first spinal level. Alternatively, the first element may comprise an agent delivery device. In such embodiments, the first element may be positionable to deliver the agent to a dorsal root ganglion or other tissue on the first spinal level.

In some embodiments, at least a portion of the first element is steerable. Alternatively or additionally, the first element may extend through a lumen in the elongate structure and be rotatable within the lumen. Likewise, the first element may be longitudinally translatable within the first opening.

In some embodiments, the elongate structure comprises a first portion having the first opening and a second portion having the second opening, wherein the first and second portions move relative to each other so as to adjust a distance between the openings. This may be useful when the first and second spinal levels are not adjacent to each other.

In some embodiments, the elongate structure includes a third opening concurrently alignable with the first spinal level and a third element extendable through the third opening and positionable so as to treat nerve tissue on the first spinal level. In such instances, the first element and third element may comprise leads each having at least one electrode and wherein the first element is positionable so as to selectively stimulate dorsal root ganglion on the first spinal level and the third element is positionable so as to selectively stimulate a different dorsal root ganglion on the first spinal level.

In another aspect of the present invention, a method is provided for delivering elements to nerve tissue on different spinal levels. In some embodiments, the method comprises advancing an elongate structure into an epidural space, wherein the elongate structure has a first opening and a second opening, and positioning the elongate structure so that the first opening substantially aligns with a first spinal level the second opening substantially aligns with a second spinal level.

In some embodiments, the method further comprises extending a first element through the first opening toward a nerve tissue on the first spinal level. When the first element comprises a lead having at least one electrode, the method may further comprise stimulating the nerve tissue on the first spinal level. In some instances, the nerve tissue comprises a dorsal root ganglion.

In some embodiments, the method further comprises manipulating the first element to direct the distal end toward the nerve tissue on the first spinal level. In some instances, manipulating comprises advancing, retracting, torqueing, curving or steering the first element.

It may be appreciated that when the first element comprises an agent delivery device, the method further comprises delivering an agent to the nerve tissue on the first spinal level.

In some embodiments, the method further comprises extending a second element through the second opening toward a nerve tissue on the second spinal level.

In some instances, the elongate structure comprises a first portion having the first opening and a second portion having the second opening. In such instances, positioning may comprise moving at least one of the portions in relation to the other. Alternatively or additionally, positioning may comprise moving the openings in relation to each other. The first and second spinal levels may or may not be adjacent to each other.

Optionally, the elongate structure may have a third opening. In such instances, positioning may comprise aligning the third opening with the first spinal level. In such instances, the method may further comprise extending a first element through the first opening toward a nerve tissue on the first spinal level and extending a third element through the third opening toward a different nerve tissue on the first spinal level. In some embodiments, the nerve tissue on the first spinal level comprises a dorsal root ganglion and the different nerve tissue on the first spinal level comprises a different dorsal root ganglion.

In yet another aspect of the present invention, a system is provided for treating nerve tissue on different spinal levels. In some embodiments, the system comprises an elongate member shaped for positioning within an epidural space, and a first lead having a lumen and at least one electrode, wherein the first lead is configured to track over the elongate member by passing the elongate member through the lumen so that the at least one electrode is positioned near a nerve tissue on a first spinal level. The elongate member may comprise a rail, rod or guidewire. In some embodiments, the system further comprises a second lead having a lumen and at least one electrode, wherein the second lead is configured to track over the elongate member by passing the elongate member through its lumen so that its at least one electrode is positioned near a nerve tissue on a second spinal level. In such instances, the first and second spinal levels may not be adjacent to each other. In some embodiments, the nerve tissue comprises a dorsal root ganglion. And, in some embodiments, the system further comprises an anchoring device configured to anchor the elongate member to a vertebrae.

In still another aspect of the present invention, a method is provided for treating nerve tissue on different spinal levels. In some embodiments, the method comprises advancing an elongate member into an epidural space, tracking a first lead having at least one electrode over the elongate member, and positioning the at least one electrode near a nerve tissue on a first spinal level. In some embodiments, the method further comprises implanting the elongate member in the epidural space. Implanting may comprise anchoring the elongate member to a vertebrae. The method may further comprise tracking a second lead having at least one electrode over the elongate member. Optionally, the method may comprise positioning the at least one electrode of the second lead near a nerve tissue on a second spinal level.

Other objects and advantages of the present invention will become apparent from the detailed description to follow, together with the accompanying drawings.

BRIEF DESCRIPTION OF THE DRAWINGS

FIG. 1A-1B, 2, 3, 4, 5 illustrate prior art.

FIGS. 9A, 9B, 9C illustrate optional adjustments of the leads within the ports.

FIG. 10 illustrates an electrode shaped to increase contact area or wrap around a nerve tissue.

FIG. 11 illustrates an electrode having a coil shape.

DETAILED DESCRIPTION OF THE INVENTION

In preferred embodiments, the devices, systems and methods stimulate the various spinal levels at specific nerve anatomies, such as the dorsal root DR or more specifically the dorsal root ganglion DRG. The following examples will illustrate specific stimulation of the dorsal root ganglia of various levels, however the embodiments are not so limited. Also, the following examples utilize various types of leads to provide stimulation. It may be appreciated that other elements, such as agent delivery devices, may be used alternatively or in addition to the leads for delivery of an agent to a specific nerve anatomy.

Figure 2:
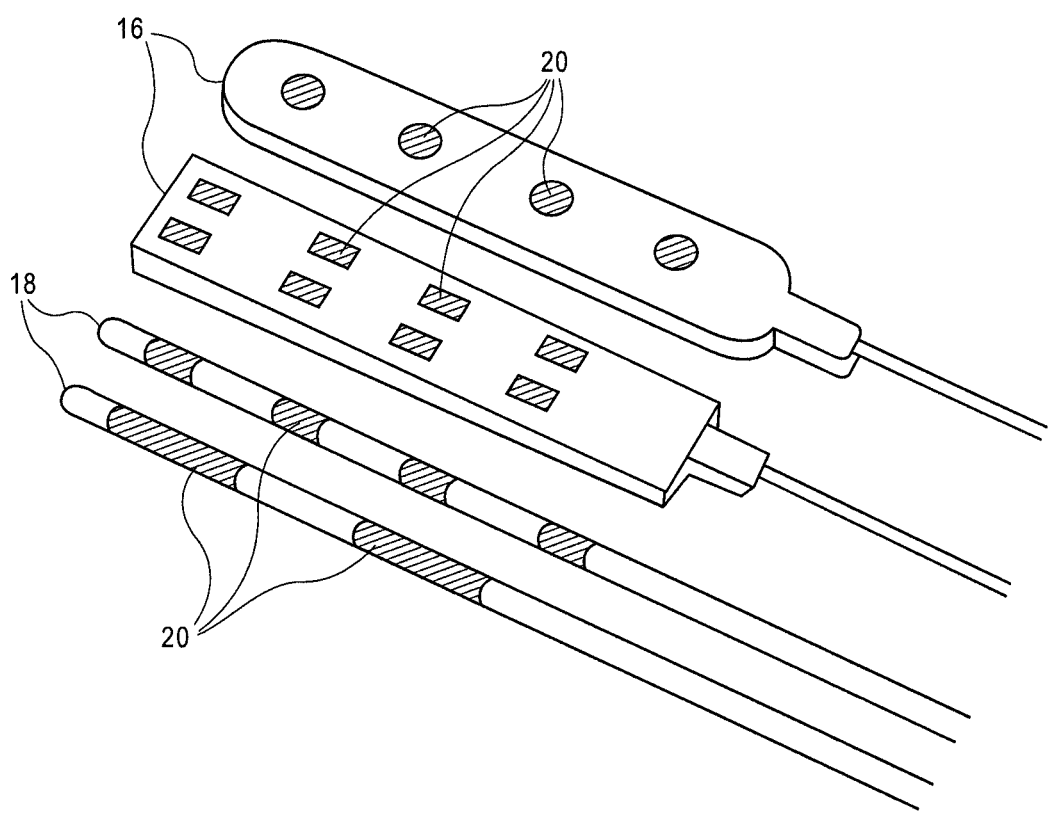
Figure 5:
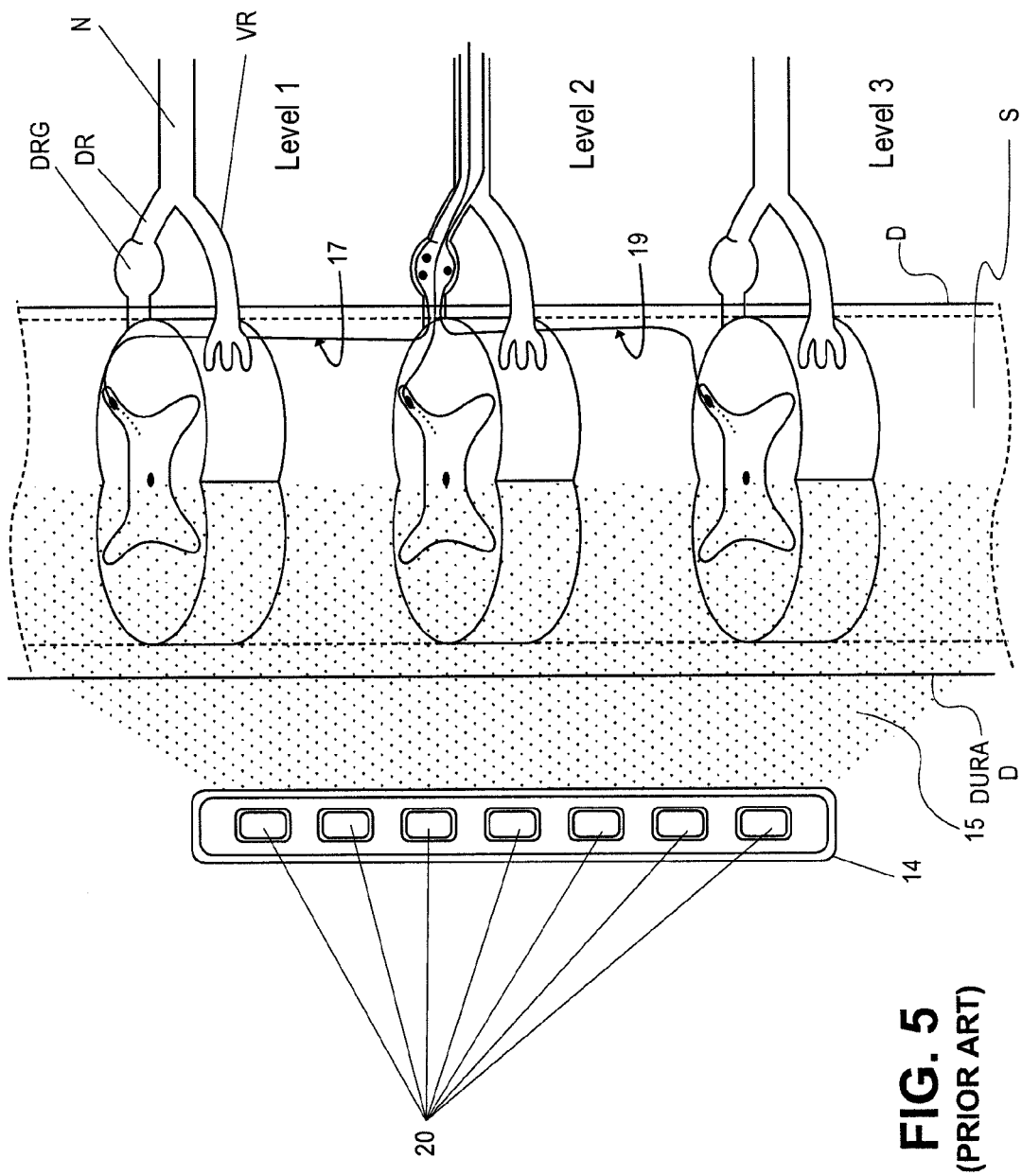
Figure 6:
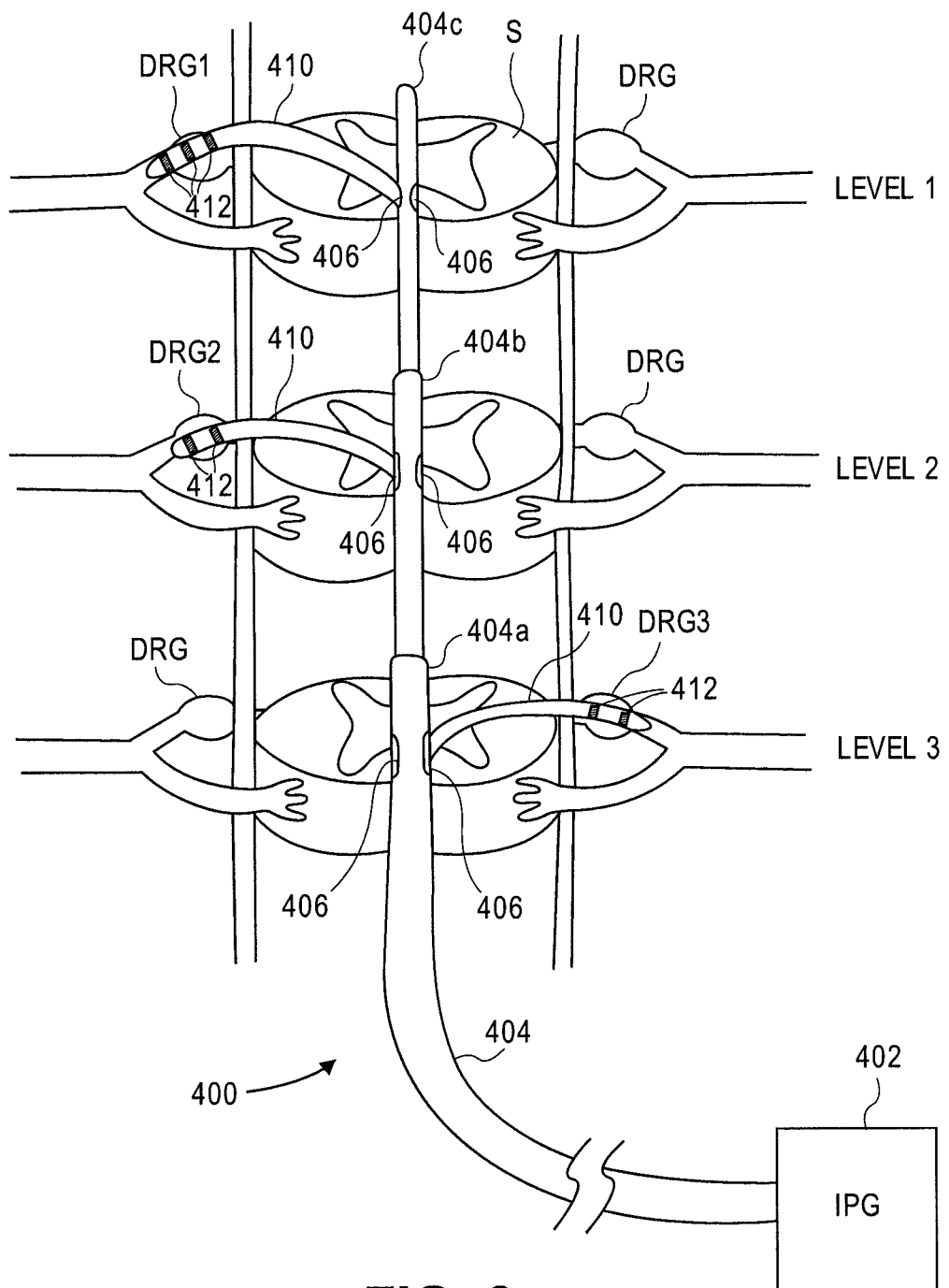
FIG. 6 illustrates positioning of a telescoping device of the present invention so as to optionally simultaneously stimulate nerve tissue on various spinal levels.

FIG. 6 illustrates positioning of a device 400 of the present invention so as to optionally simultaneously stimulate various levels (levels 1, 2, 3 in this example) of the spinal cord S. The device 400 is shown positioned within an epidural space of the spinal column, residing against the dura layer of the spinal cord. This is achieved by inserting the device through the skin via an epidural needle. FIG. 6 illustrates the device 400 positioned via an antegrade approach, however it may be appreciated that a retrograde approach may also be used.

In this embodiment, the device 400 comprises an elongate structure or shaft 404 wherein the shaft 404 has a first opening or port 406 which is alignable with a first spinal level and a second opening or port 406 which is concurrently alignable with a second spinal level. More particularly, in this embodiment the shaft 404 is telescoping (for example, three telescoping portions 404a, 404b, 404c are shown). Each telescoping portion includes at least one opening or port 406 and at least one lumen configured to allow passage of at least one element, such as a lead 410, through the opening or port 406. The ports 406 face lateral to a midline of the epidural space so that the lead 410 may be advanced away from the midline in a lateral direction, such as toward a DRG. In some embodiments, each telescoping portion includes two ports, one on each side, so that each faces an opposite direction on the same spinal level. This provides simultaneous access to DRGs on the same spinal level on both sides of the spinal cord. Typically, ports 406 are located on various telescoping portions so that the distance between the ports 406 may be adjusted by moving the telescoping portions relative to each other (e.g. retracting or advancing). Thus, the ports 406 are alignable with various spinal levels so that nerve tissue can be simultaneously accessed on multiple spinal levels.

The telescoping portions 404a, 404b, 404c may be comprised of various materials, preferably a flexible polymer. The portions 404a, 404b, 404c may be supported by a stylet during placement. The telescoping portions 404a, 404b, 404c may have various cross-sectional shapes, including flat (which may be oval, rectangular, etc) and thick (which may be circular, square, etc).

As mentioned, one or more elements, such as leads 410, are advanceable through the shaft 404 so that each lead 410 exits a port 406 and is advanceable toward a target tissue, such as a DRG. Each lead 410 includes one or more electrodes 412, and the lead 410 is positionable so that the one or more electrodes 412 are desirably positioned in, on, or about the DRG. Such positioning may include manipulation such as advancing, retracting, torqueing, curving or steering the lead 410. Some examples of such manipulations will be described later in relation to FIGS. 9A-9C and are applicable to this embodiment as well. This may be repeated for positioning of additional leads 410 at the same level or other levels.

The device 400 is electrically connected to a power source or implantable pulse generator (IPG) 402, as shown, which is implanted in the body of the patient. The IPG 402 provides stimulation energy to the electrodes 412. Thus, in FIG. 6, the device 400 is shown extending longitudinally along the spinal column and leads 410 are shown extending to a DRG at level 1 (DRG1), a DRG at level 2 (DRG2) and a DRG at level 3 (DRG3). Thus, the device 400 extends across multiple levels in the form of a grouped lead providing a single extension to the IPG 402. DRG1, DRG2, DRG3 can be stimulated simultaneously or in any pattern which provides the most desirable therapeutic result, such as pain management.

Figure 7:
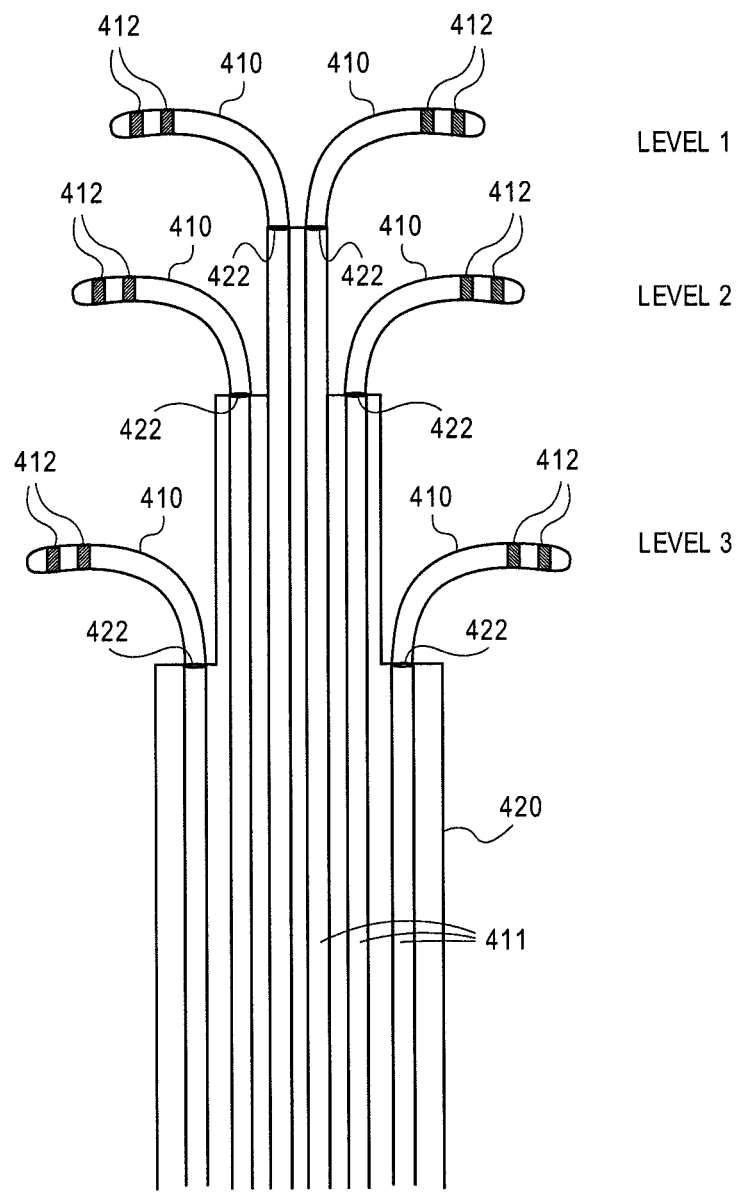
FIG. 7 illustrates a non-telescoping device of the present invention used to optionally simultaneously stimulate nerve tissue on various spinal levels.

FIG. 7 illustrates another embodiment of a device 400 of the present invention for delivering leads 410 so as to optionally simultaneously stimulate various levels (levels 1, 2, 3 in this example) of the spinal cord S. Again, the device 400 comprises an elongate structure or shaft 420 shaped for positioning within an epidural space. The shaft 420 has a first opening or port 422 alignable with a first spinal level and a second opening or port 422 alignable with a second spinal level. In this embodiment, the shaft 420 is non-telescoping so the distance between the ports 422 is fixed. Typically, the ports 422 are spaced so as to align with spinal levels of the average population. However, it may be appreciated that a variety of shafts 420 may be provided with different port 422 spacing to allow the practitioner the option of choosing the most appropriate spacing for the individual patient. In this embodiment, the ports 422 face longitudinal to a midline of the epidural space. However, it may be appreciated that the ports 422 may alternatively face lateral to the midline of the epidural space.

The elongate structure or shaft 420 includes at least one lumen 411 configured to allow passage of at least one element, such as a lead 410, through a port 422 toward nerve tissue on a desired spinal level. To position an individual lead 410 having at least one electrode 412 thereon near a target DRG, the shaft 420 is positioned so that a port 422 is desirably aligned with the target DRG. The lead 410 is then advanced through the shaft 420 so that the lead 410 exits the aligned port 422 and advances toward the target DRG. The lead 410 is then positioned so that the one or more electrodes 412 are desirably positioned in, on, or about the DRG. Such positioning may include manipulation such as advancing, retracting, torqueing, curving or steering the lead 410. Some examples of such manipulations will be described later in relation to FIGS. 9A-9C and are applicable to this embodiment as well. Such manipulation may also compensate for any differences in anatomical spacing of the levels of the spinal cord S. This may be repeated for positioning of additional leads 410 at the same level or other levels. Optionally, this embodiment of the device 400 may be adapted to be telescoping.

Figures 8A, 8B, 8C:
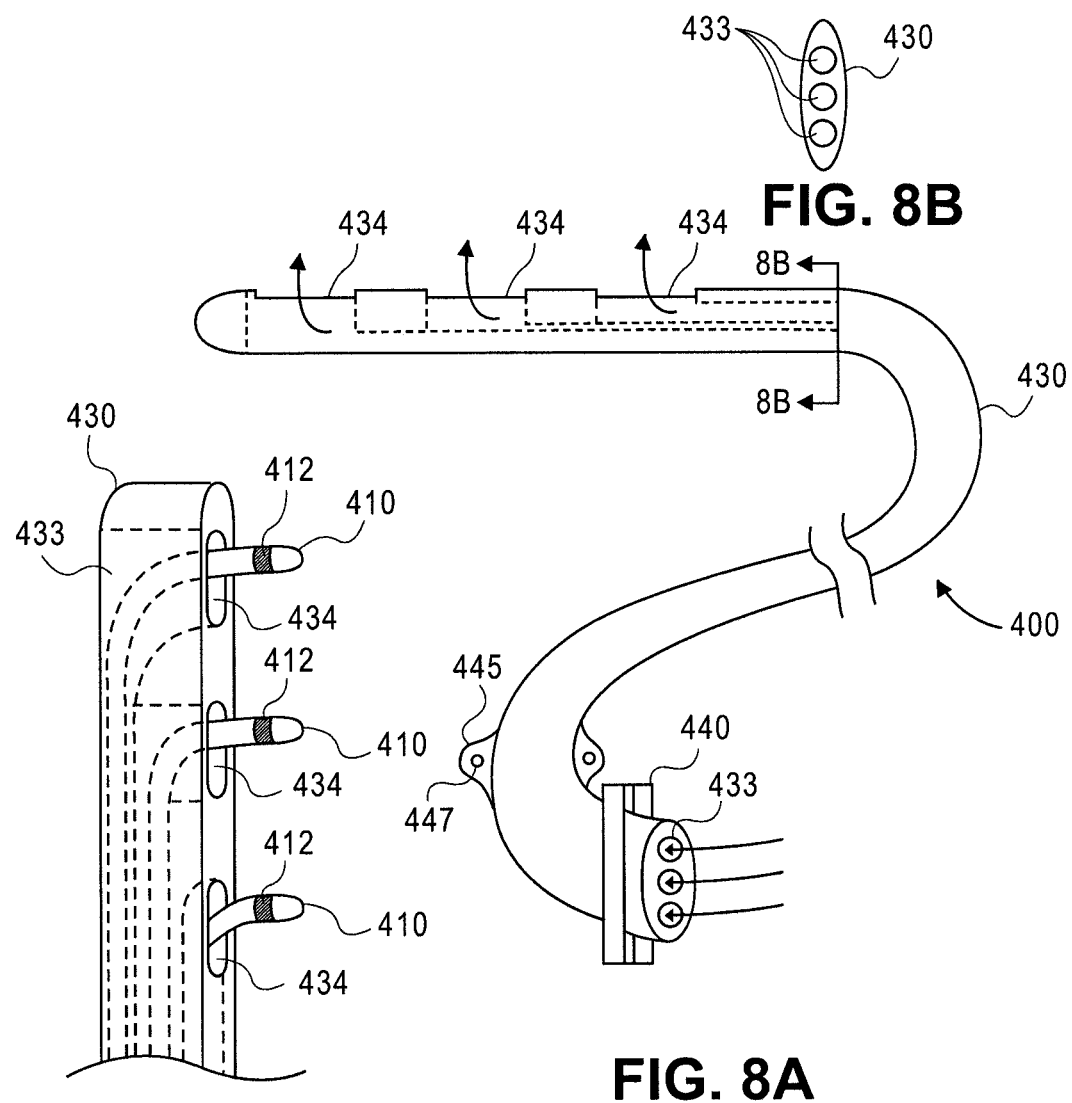
FIGS. 8A, 8B, 8C illustrate an embodiment of a grouped lead device having an elongate structure which allows advancement of leads through slots or ports.

FIGS. 8A-8C illustrate another embodiment of a grouped lead device 400. In this embodiment, the device 400 comprises an elongate structure or shaft 430 shaped for positioning within an epidural space. The shaft 430 includes at least one lumen 433 configured to allow passage of at least one element, such as a lead 410, and at least one opening, slot or port 434 which allows advancement of leads 410 through the slots or ports 434. Individual leads 410 may be advanced through lumens 433 in the structure 430 and exit through ports 434 disposed near its distal end 436. In this embodiment, the leads 410 each include at least one electrode 412 for stimulating the anatomy, particularly the DRG. In this embodiment, the structure 430 has a flat cross-section (FIG. 8B) wherein the lumens 433 extend in parallel within the structure 430 and the ports 434 are aligned along the side of the structure (FIG. 8C). It may be appreciated that the ports 434 may be aligned along one or both sides of the structure to allow access to DRGs on either side of the spinal cord S. Again, axial distances between the ports 434 are designed to generally direct the leads 410 toward the target DRGs. Adjustment of the actual distances between the leads 410 can be made by movement of the leads 410 within the lumens 433 (advancement, retraction, torquing, etc.).

FIGS. 9A-9C illustrate optional adjustments of the leads 410 within the ports 434. Typically the leads 410 will be pre-shaped so as to extend through the ports 434 at an angle. Various angles may be achieved by using leads 410 having different pre-set curvatures. In some embodiments, angular adjustment of the distal end of the lead 410 (FIG. 9A) can be made with the use of a pullwire. Axial movement (FIG. 9B) can be achieved by advancing and retracting the leads 410 within the lumens 433. Radial movement (FIG. 9C) can be achieved by rotating or torquing the leads 410 within the lumens 433.

The leads 410 described herein may include one or more electrodes 412 of various designs. Typically, the electrodes 412 are illustrated as cuff or band electrodes extending around the lead 410. It may be appreciated that the electrodes 412 may have a variety of shapes and sizes including a pointed tip which is used to contact or pierce a tissue, an array along a flat portion of a lead, an array at least partially extending around the circumference of a lead, etc. FIGS. 10-11 illustrate some alternative embodiments of electrodes 412 that may be used with the present invention. The distal end of the lead 410 or the electrode 412 may be shaped so as to increase contact area or wrap around the DRG (FIG. 10). Or, the electrode 412 may have other shapes, such as a coil (FIG. 11). These designs may also improve anchoring of the lead 410 to the target tissue.

Referring back to FIG. 8A, once the lead 410 positions have been desirably adjusted, the leads 410 are fixed in place with the use of a fixing mechanism 440. In some embodiments, the mechanism 440 clamps the slotted structure 430 so as to hold the leads 410 in place by frictional forces. Other fixation mechanisms may alternatively be used. The leads 410 are connected with an IPG 402 which is implanted in the body of the patient. The IPG 402 provides stimulation energy to the electrodes 412. Typically, the slotted structure or shaft 430 is anchored to tissue near the IPG or along the shaft 430 outside of the spinal column. This assists in reducing any possible migration or movement. Thus, in some embodiments, the shaft 430 includes a tissue anchor 445 which may be used to anchor the shaft 430 to the surrounding tissue. In this example, the tissue anchor 445 includes at least one suture hole 447 through which suture may be passed to suture the anchor 445 to the tissue.

The previously described embodiments of devices 400 of the present invention are described and illustrated to be positionable within an epidural space, such as along the midline of the spinal column or at any distance from the midline along the spinal column. Optionally, these and other embodiments of the devices 400 may be positioned within the epidural space at a distance from the midline which aligns the elongate structure with the dorsal root ganglions. Such placement is illustrated in FIG. 12, wherein a cross-section of the elongate structure 200 is shown positioned near a DRG on a single spinal level.

Figure 12:
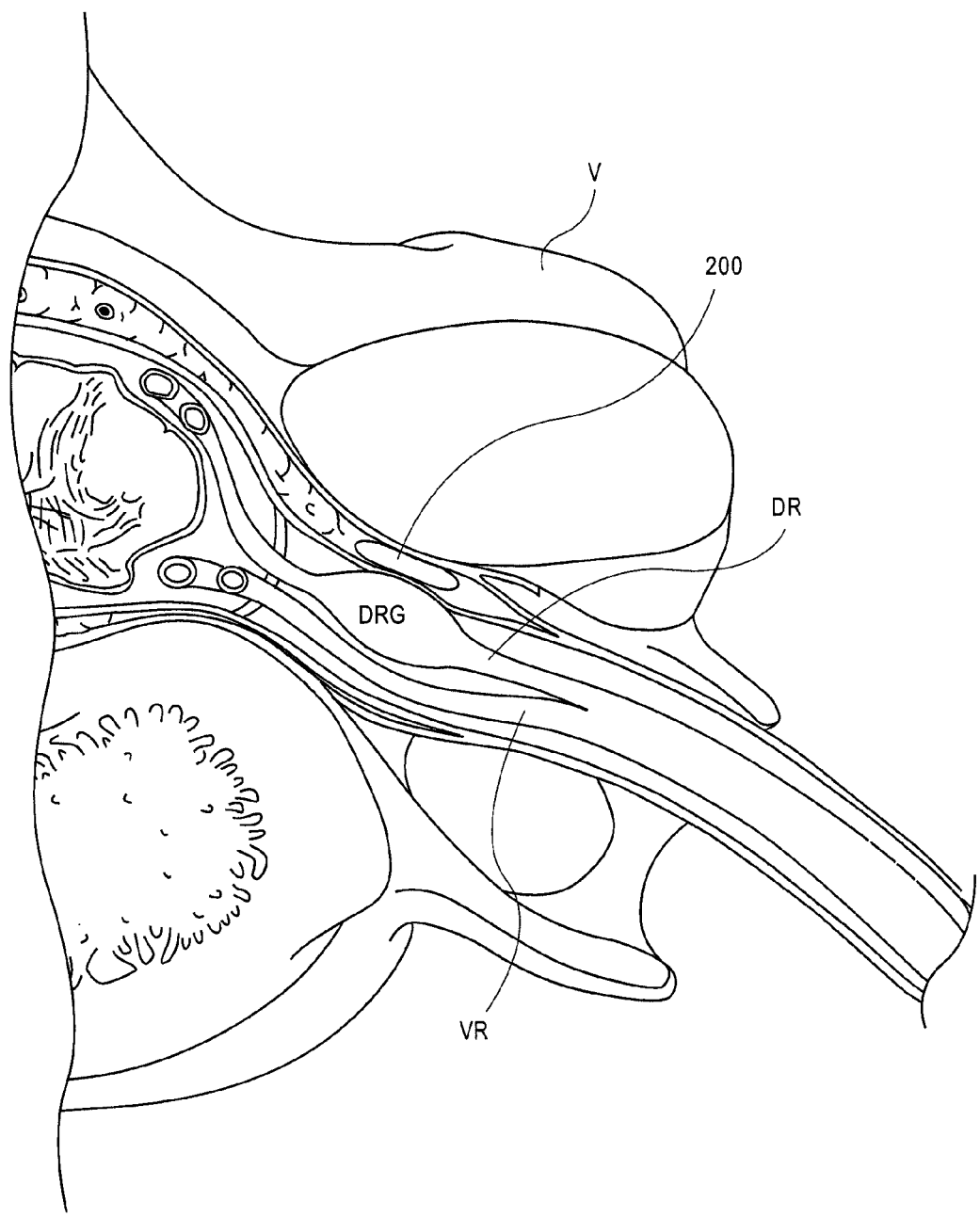
FIG. 12 illustrates a cross-sectional view of an elongate structure of the present invention positioned near a DRG on a single spinal level.
Figure 13:
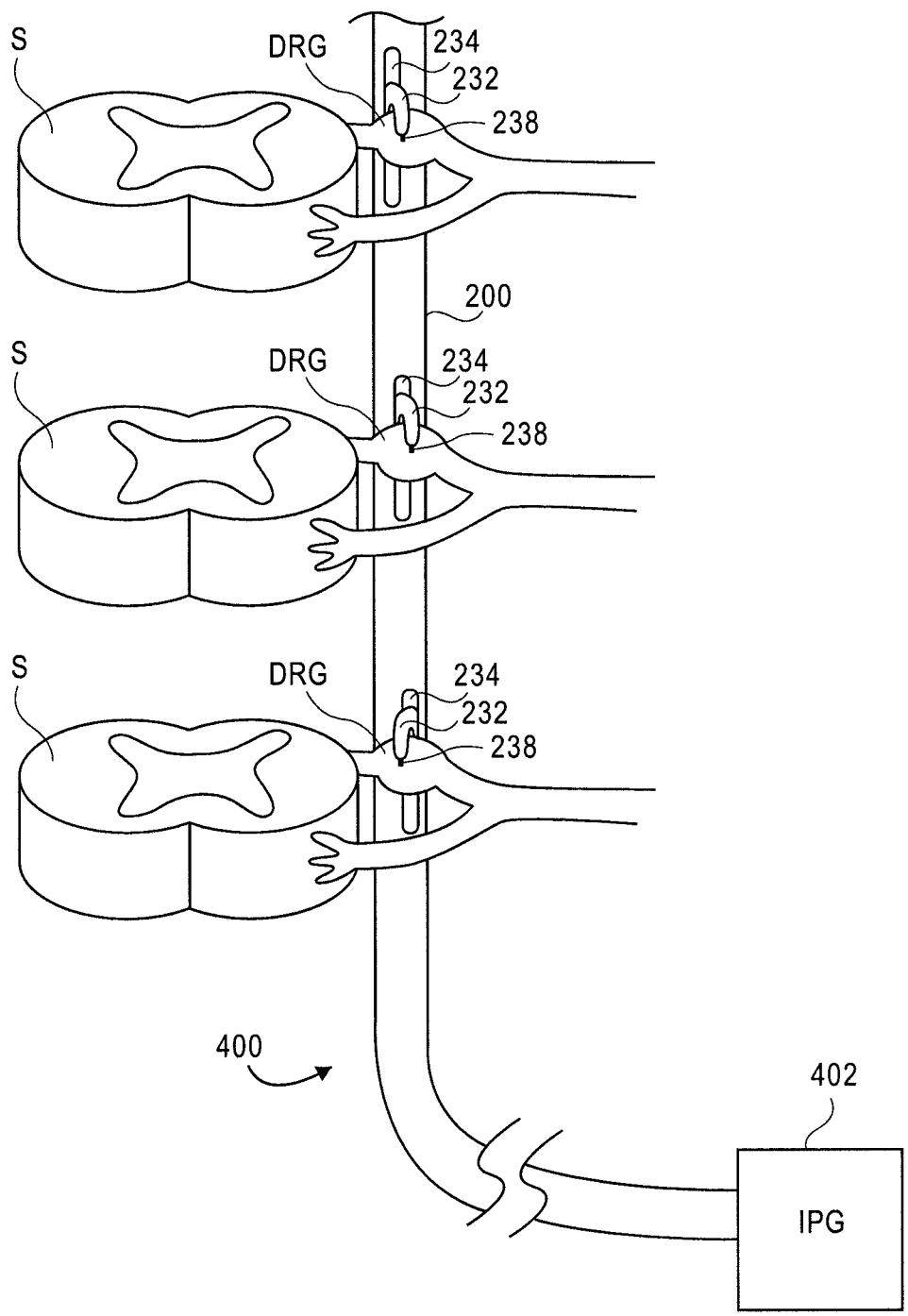
FIG. 13 illustrates a side view of the device of FIG. 12 shown extending between multiple spinal levels.

FIG. 13 illustrates an embodiment of a device 400 of the present invention positioned as illustrated in FIG. 12. As shown, the device 400 comprises an elongate structure 200 extending longitudinally through the foramens of each vertebrae V. It may be appreciated that the elongate structure 200 may be positioned at a variety of locations adjacent or near the DRG while maintaining the longitudinal orientation. As shown, the structure 200 allows advancement of multiple leads 232 therethrough so that each lead 232 is able to stimulate a DRG on an individual level. Thus, DRGs on multiple spinal levels may be simultaneously stimulated or stimulated in any pattern which provides the most desirable therapeutic result. The structure 200 also provides a single extension to an IPG 402.

Figures 14A, 14B:
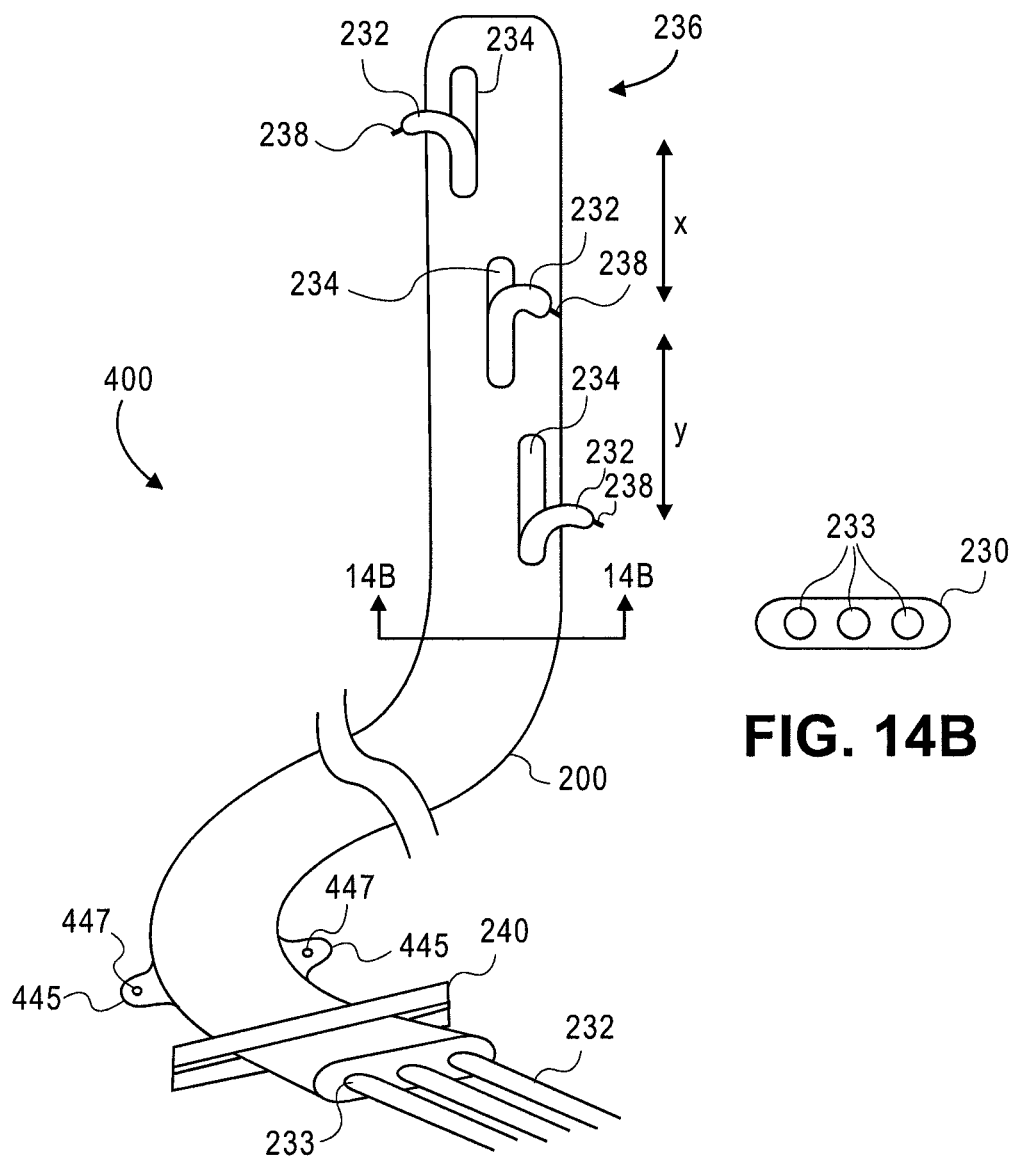
FIGS. 14A-14B provide a more detailed view of the device of FIG. 13.

FIGS. 14A-14B provide a more detailed view of the device 400 of FIG. 13. As shown, the structure 200 includes at least one lumen 233 configured to allow passage of at least one element, such as a lead 232 through an opening, ports or slots 234 toward a nerve tissue on a spinal level. FIG. 14A illustrates individual leads 232 advanced through lumens 233 in the slotted structure 200 and exiting through slots 234 disposed near its distal end 236. In this embodiment, the leads 232 each have an electrode tip 238 for stimulating the anatomy, particularly the DRG. The electrode tips 238 of the lead may have a variety of designs, such as a pointed tip which is used to contact or pierce a tissue. Alternatively or in addition, the leads may include electrodes mounted thereon, such as in an array. Or, the tip 238 may be shaped so as to increase contact area or wrap around the DRG (such as illustrated in FIG. 10). Or, the tip may have other shapes, such as a coil (FIG. 11). It may also be appreciated that the structure 200 may be disposed in an antegrade position or retrograde position.

In this embodiment, the slotted structure 200 has a flat cross-section (FIG. 14B) wherein the lumens 233 extend in parallel within the structure 200 and the slots 234 are arranged in a staggered fashion across the face of the slotted structure 200 corresponding to the position of the lumens 233. Axial distances between the slots 234 are designed to generally direct the leads toward the target DRGs on each spinal level. Adjustment of the actual distance between the leads (X & Y) can be made by movement of the leads 232 within the lumens 233 (advancement, retraction, torquing, etc.), such as illustrated in FIGS. 9A-9C.

Once the lead 232 positions have been desirably adjusted, the leads 232 may be fixed in place with the use of a fixing mechanism 240. In this embodiment, the mechanism 240 clamps the slotted structure 200, as illustrated in FIG. 14A, so as to hold the leads 232 in place by frictional forces. Other fixation mechanisms may alternatively be used.

Typically, the slotted structure or shaft 200 is anchored to tissue near the IPG or along the shaft 200 outside of the spinal column. This assists in reducing any possible migration or movement. Thus, in some embodiments, the shaft 200 includes a tissue anchor 445 which may be used to anchor the shaft 200 to the surrounding tissue. In this example, the tissue anchor 445 includes at least one suture hole 447 through which suture may be passed to suture the anchor 445 to the tissue. Optionally, the structure 200 may be fixed to one or more vertebrae.

Figure 15:
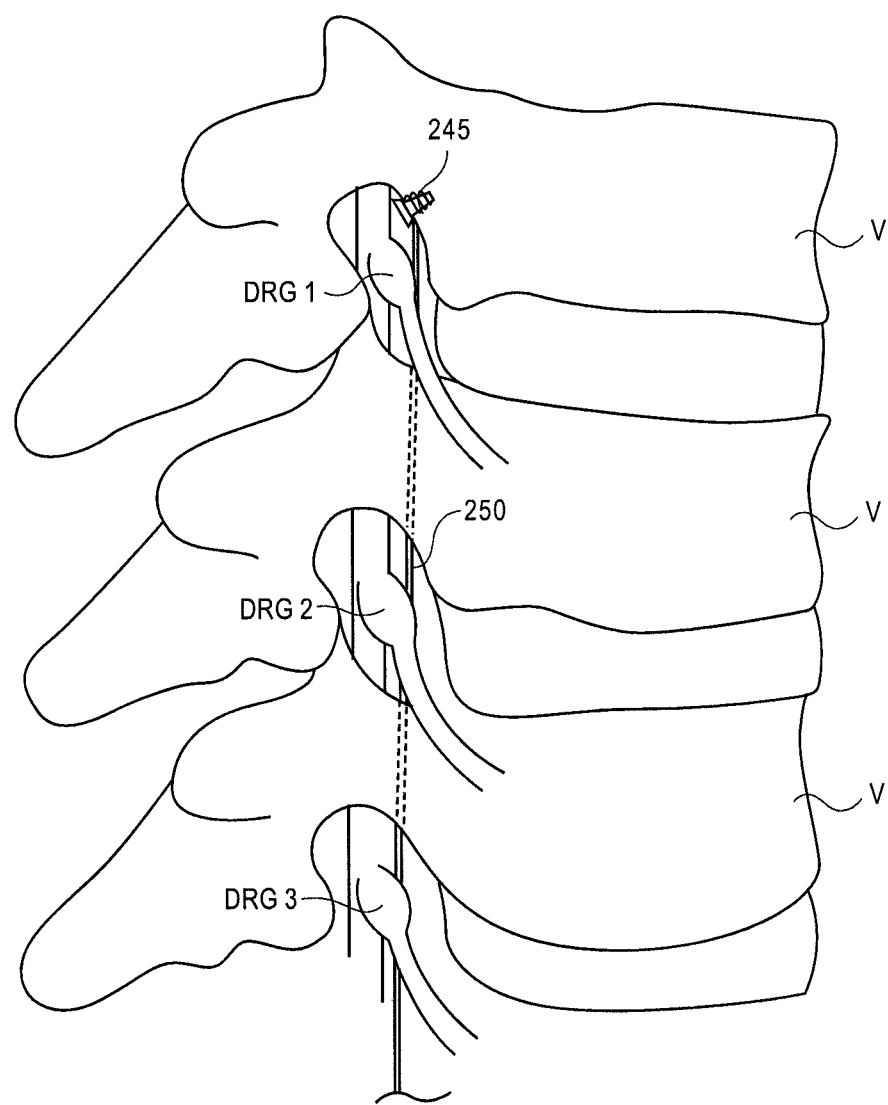
FIG. 15 illustrates the placement of a rail, rod, guidewire or other elongate member or structure in an epidural space, particularly longitudinally through the foramens of each vertebrae.
Figure 16:
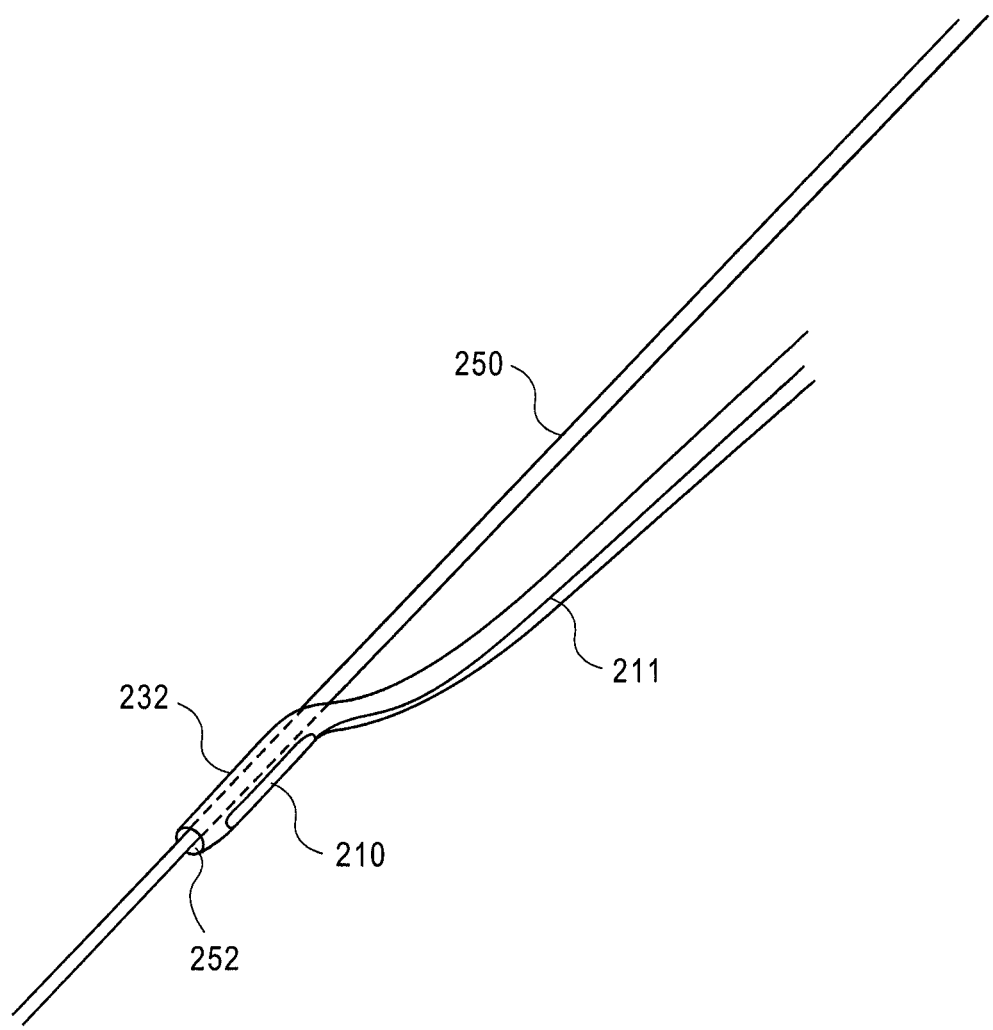
FIG. 16 illustrates individual leads, each including a lumen extending through at least a portion of the lead that is used for tracking over a structure.
Figure 17:
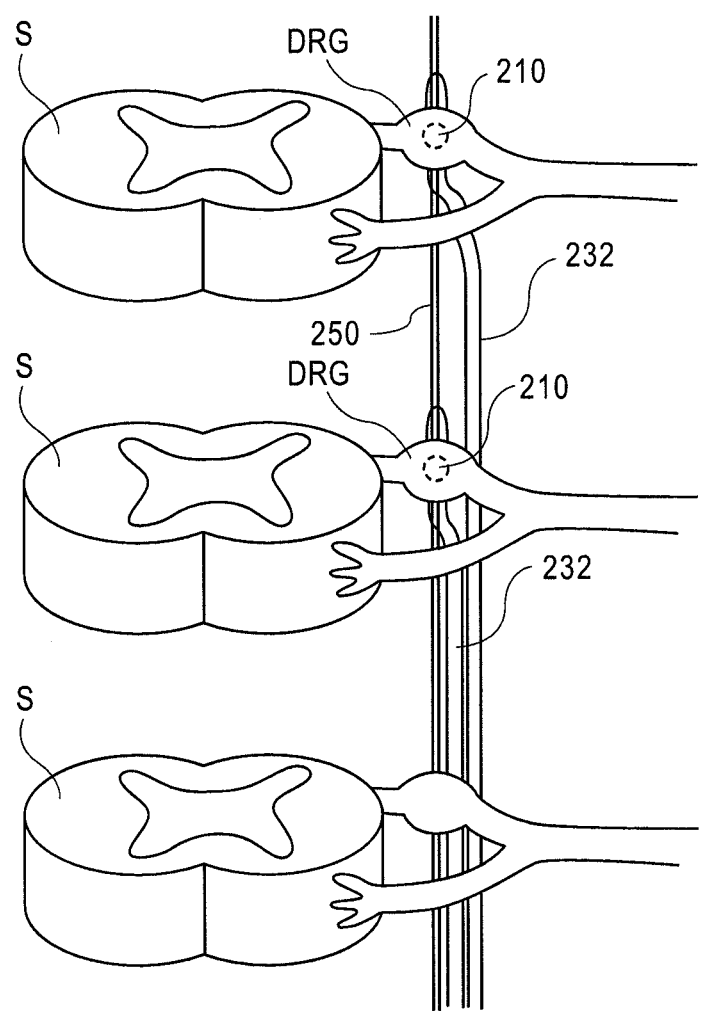
FIG. 17 illustrates a plurality of leads tracked over a structure, each lead positioned in a target location near a DRG.

FIGS. 15-17 illustrate another embodiment of a grouped lead system 200 which allows individual placement of leads 232 at various levels while grouping the leads near the proximal end so as to extend out in a bundle to an IPG. FIG. 15 illustrates the placement of a rail, rod, guidewire or other elongate member or structure 250 in an epidural space, particularly longitudinally through the foramens of each vertebrae V. It may be appreciated that the elongate member or structure 250 may be positioned at a variety of locations adjacent or near the DRG while maintaining the longitudinal orientation.

The structure 250 is used to advance individual leads 232 into desired positions near the DRGs or target anatomy. The structure 250 is typically anchored to a vertebrae V as shown, such as with an anchoring device 245, such as a bone tack or bone screw. Referring to FIG. 16, each individual lead 232 includes a lumen 252 extending through at least a portion of the lead 232 that is used for tracking over the structure 250. Each lead also includes at least one electrode 210 which is electrically connected to a conductive wire 211 which extends to a power source or IPG. FIG. 17 illustrates a plurality of leads 232 tracked over the structure 250, each lead 232 positioned in a target location near a DRG. It may be appreciated that any number of leads 232 may be advanced over the same structure 250. Further, it may be appreciated that any number of structures 250 may be anchored in various locations for tracking leads to any desired location along the spinal column. The one or more structures 250 may then be left in place to support the leads 232.

The above embodiments describe devices, systems and methods that utilize that directly stimulates the dorsal root, particularly the dorsal root ganglion (DRG), while minimizing or excluding undesired stimulation of other anatomies. In some embodiments, this allows access to multiple levels of the spinal column with the use of a single device. This reduces procedure complexity, time and recovery since a single access path is created rather than individual access paths to each level of the spinal column. These embodiments also have a reduced number of paths to an IPG. It may be appreciated that the devices, systems and methods of the present invention may also be used to stimulate other portions of the spinal anatomy or other anatomies.

Although the foregoing invention has been described in some detail by way of illustration and example, for purposes of clarity of understanding, it will be obvious that various alternatives, modifications and equivalents may be used and the above description should not be taken as limiting in scope of the invention.

What is claimed is:

1. A delivery device for delivering elements to nerve tissue on different spinal levels, the device comprising:
    a shaft shaped for positioning within an epidural space, wherein the shaft has a first portion having a first opening in the shaft and a second portion having a distal opening and a second opening in the shaft, wherein the first portion is able to move telescopically through the distal opening so as to move the first opening beyond and relative to the second portion so as to adjust the distance between the first and second openings so as to concurrently align the first opening with a first spinal level and the second opening with a second spinal level, and
    wherein the shaft includes at least one lumen configured to allow passage of at least one element through the first opening toward nerve tissue on the first spinal level and passage of at least one element through the second opening toward nerve tissue on the second spinal level, wherein the at least one element comprises a lead or an agent delivery device.

2. A delivery device as in claim 1, wherein the first and second spinal levels are not adjacent to each other.

3. A delivery device as in claim 1, wherein the openings face lateral to a midline of the epidural space.

4. A delivery device as in claim 1, wherein the first opening faces a direction on the first spinal level and another opening faces in a substantially opposite direction on the first spinal level.

5. A delivery device as in claim 1, wherein the openings face longitudinal to a midline of the epidural space.

6. A delivery device as in claim 1, wherein the at least one lumen comprises an individual lumen extending to the first opening and an individual lumen extending to the second opening.

7. A delivery device as in claim 1, wherein the first opening is shaped to allow longitudinal translation of the at least one element within the first opening.

8. A delivery device as in claim 7, wherein the first opening has an oblong shape.

9. A delivery device as in claim 1, further comprising a mechanism to fix the at least one element in relation to the shaft.

10. A device as in claim 1, wherein the nerve tissue on the first spinal level comprises a first dorsal root ganglion.

11. A device as in claim 1, wherein the nerve tissue on the second spinal level comprises a second dorsal root ganglion.

12. A device as in claim 1, wherein the nerve tissue on the first spinal level comprises a first dorsal root ganglion and the nerve tissue on the second spinal level comprises a second dorsal root ganglion.

13. A device as in claim 1, wherein the shaft includes a third opening concurrently alignable with the first spinal level.

14. A device as in claim 13, wherein the shaft allows passage of a third element through the third opening so as to treat other nerve tissue on the first spinal level.

15. A device as in claim 14, wherein the nerve tissue on the first spinal level comprises a dorsal root ganglion and the other nerve tissue on the first spinal level comprises another dorsal root ganglion on the first spinal level.

16. A device as in claim 1, wherein at least one of the portions is comprised of a flexible polymer.

17. A device as in claim 1, wherein at least one of the portions is supportable by a stylet during placement.

18. A device as in claim 1, wherein at least one of the portions has an oval or rectangular shape.

19. A device as in claim 1, wherein at least one of the portions has a circular or square shape.

20. A system as in claim 1, wherein the shaft includes a tissue anchor to anchor the shaft to surrounding tissue.

21. A system for treating nerve tissue on different spinal levels, the system comprising:
    a shaft shaped for positioning within an epidural space, wherein the shaft has a first portion having a first opening in the shaft and a second portion having a distal opening and a second opening in the shaft, wherein the first portion is able to move telescopically through the distal opening so as to move the first opening beyond and relative to the second portion so as to adjust the distance between the first and second openings so as to concurrently align the first opening with a first spinal level and the second opening with a second spinal level, and
    wherein the shaft includes at least one lumen configured to allow passage of at least one element through the first opening toward nerve tissue on the first spinal level and passage of at least one element through the second opening toward nerve tissue on the second spinal level, wherein the at least one element comprises a lead or an agent delivery device;
    a first element extendable through the first opening and positionable so as to treat nerve tissue on the first spinal level; and
    a second element extendable through the second opening and positionable so as to treat nerve tissue on the second spinal level.

22. A system as in claim 21, wherein the first element comprises a lead having at least one electrode.

23. A system as in claim 22, wherein the first element is positionable so as to selectively stimulate a dorsal root ganglion on the first spinal level.

24. A system as in claim 21, wherein the second element comprises a lead having at least one electrode.

25. A system as in claim 24, wherein the second element is positionable so as to selectively stimulate a dorsal root ganglion on the first spinal level.

26. A system as in claim 21, wherein the first and/or second element comprises an agent delivery device.

27. A system as in claim 21, wherein at least one of the elements is steerable.

28. A system as in claim 21, wherein at least one of the elements extends through a lumen in the shaft and wherein the at least one of the elements is rotatable within the lumen.

29. A system as in claim 21, wherein at least one of the elements is longitudinally translatable within its associated opening.

30. A system as in claim 21, wherein the first and second spinal levels are not adjacent to each other.

31. A system as in claim 21, wherein the elongate structure includes a third opening concurrently alignable with the first spinal level and a third element extendable through the third opening and positionable so as to treat nerve tissue on the first spinal level.

32. A system as in claim 31, wherein the first element and third element comprise leads each having at least one electrode and wherein the first element is positionable so as to selectively stimulate dorsal root ganglion on the first spinal level and the third element is positionable so as to selectively stimulate a different dorsal root ganglion on the first spinal level.

33. A system as in claim 21, wherein at least one of the elements comprises a lead having one or more electrodes comprising a pointed tip which is used to contact or pierce tissue.

34. A system as in claim 21, wherein at least one of the elements comprises a lead having one or more electrodes comprising an array along a flat portion of the lead.

35. A system as in claim 21, wherein at least one of the elements comprises a lead having one or more electrodes comprising an array at least partially extending around the circumference of the lead.

36. A system as in claim 21, wherein at least one of the elements comprises a lead having a distal end or electrode shaped so as to wrap around a dorsal root ganglion.

37. A system as in claim 21, wherein at least one of the elements comprises a lead having an electrode having a coil shape.

38. A system as in claim 21, further comprising a mechanism to fix at least one element in relation to the shaft.

39. A system as in claim 21, wherein the shaft includes a tissue anchor to anchor the shaft to surrounding tissue.

* * * * *